US012721903B2

(12) United States Patent
Kanai et al.

(10) Patent No.: US 12,721,903 B2
(45) Date of Patent: Sep. 1, 2026

(54) CONJUGATE OF PHTHALOCY ANINE DYE AND ANTIBODY OR PEPTIDE

(71) Applicants: THE UNIVERSITY OF TOKYO, Tokyo (JP); COMPLECURE, INC., Tokyo (JP)

(72) Inventors: Motomu Kanai, Tokyo (JP); Kenzo Yamatsugu, Tokyo (JP); Toshifumi Tatsumi, Tokyo (JP); Kazuki Takahashi, Tokyo (JP); Tatsuhiko Kodama, Tokyo (JP); Akira Sugiyama, Tokyo (JP); Masanobu Tsukagoshi, Tokyo (JP); Yuzo Toda, Tokyo (JP)

(73) Assignees: THE UNIVERSITY OF TOKYO, Tokyo (JP); COMPLECURE, INC., Tokyo (JP)

( * ) Notice: Subject to any disclaimer, the term of this patent is extended or adjusted under 35 U.S.C. 154(b) by 973 days.

(21) Appl. No.: 17/795,719

(22) PCT Filed: Feb. 4, 2021

(86) PCT No.: PCT/JP2021/004100

§ 371 (c)(1),
(2) Date: Jul. 27, 2022

(87) PCT Pub. No.: WO2021/157655

PCT Pub. Date: Aug. 12, 2021

(65) Prior Publication Data

US 2023/0125454 A1 Apr. 27, 2023

(30) Foreign Application Priority Data

Feb. 5, 2020 (JP) ................................ 2020-017910

(51) Int. Cl.
*A61K 47/68* (2017.01)
*A61K 47/55* (2017.01)
(Continued)

(52) U.S. Cl.
CPC .......... *A61K 47/6851* (2017.08); *A61K 47/55* (2017.08); *A61K 47/6803* (2017.08); *A61P 35/00* (2018.01); *C09B 47/30* (2013.01)

(58) Field of Classification Search
CPC ..... A61P 35/00; A61K 47/55; A61K 47/6803; A61K 47/6851; A61K 41/0071;
(Continued)

(56) References Cited

U.S. PATENT DOCUMENTS

| | | | | |
|---|---|---|---|---|
| 5,824,799 A | | 10/1998 | Buechler et al. | |
| 12,115,223 B2 | * | 10/2024 | Kanai | A61K 47/6853 |

(Continued)

FOREIGN PATENT DOCUMENTS

| | | | |
|---|---|---|---|
| CN | 10345639 | A | 12/2013 |
| CN | 105669735 | A | 6/2016 |

(Continued)

OTHER PUBLICATIONS

Peng, Xinzhan, et al. "Phthalocyanine Dye as an Extremely Photostable and Highly Fluorescent Near-Infrared Labeling Reagent." Proceedings vol. 6097, Optical Molecular Probes for Biomedical Applications, 2006, p. 60970E-1. DOI.org (Crossref), https:// doi.org/10. 1117/12.669173. (Year: 2006).*

(Continued)

*Primary Examiner* — Clinton A Brooks
*Assistant Examiner* — Kyle Nottingham
(74) *Attorney, Agent, or Firm* — GREENBLUM & BERNSTEIN, P.L.C.

(57) ABSTRACT

A phthalocyanine dye for use in photoimmunotherapy, and a method for producing it, and a conjugate of the phthalocyanine dye and an antibody or a peptide are provided, including—a compound represented by formula (1) or a salt thereof:

(1)

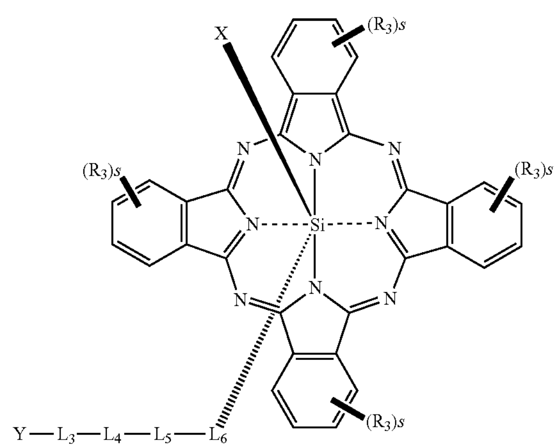

wherein X represents a substituent having a hydrophilic group at the terminus thereof; $L_3$, $L_4$, $L_5$, and $L_6$ each independently represent a divalent linking group; Y represents a group capable of binding to an antibody or a peptide; $R_3$ represents a substituent, such as an alkyl group containing 1 to 6 carbon atoms, an alkoxy group containing 1 to 6 carbon atoms, a halogen atom, —$SR_{11}$, —$SOR_{12}$, an aryl group containing 6 to 10 carbon atoms, —$N(R_{13})(R_{14})$, or —$NO_2$, wherein when a plurality of $R_3$s are present, the plurality of $R_3$s may be identical to or different from one another; and s represents an integer of 0 to 4.

8 Claims, 6 Drawing Sheets

(51) Int. Cl.
*A61P 35/00* (2006.01)
*C09B 47/30* (2006.01)

(58) Field of Classification Search
CPC .... A61K 47/54; A61K 47/6855; C09B 47/30; C09B 47/08; C09B 69/008; C07D 487/22; C07F 7/10; C07K 5/0806; C07K 16/32
See application file for complete search history.

(56) References Cited

U.S. PATENT DOCUMENTS

| | | | |
|---|---|---|---|
| 2017/0281789 | A1 | 10/2017 | Basilion et al. |
| 2022/0016245 | A1 | 1/2022 | Kanai et al. |

FOREIGN PATENT DOCUMENTS

| | | | |
|---|---|---|---|
| CN | 106573054 | A | 4/2017 |
| CN | 106866721 | A | 6/2017 |
| CN | 107226839 | A | 10/2017 |
| CN | 111166882 | A | 5/2020 |
| JP | 2017-524659 | A | 9/1998 |
| JP | H10-508897 | A | 9/1998 |
| JP | 2014-523907 | A | 9/2014 |
| JP | 6127045 | B2 | 5/2017 |
| JP | 2018-528268 | A | 9/2018 |
| JP | 2021-054739 | A | 4/2021 |
| WO | 96/029367 | A1 | 9/1996 |
| WO | 2013/009475 | A1 | 1/2013 |
| WO | 2015/125820 | A1 | 8/2015 |
| WO | 2015/187677 | A1 | 12/2015 |
| WO | 2017/031367 | A1 | 2/2017 |
| WO | 2020/060260 | A1 | 3/2020 |
| WO | 2020/138427 | A1 | 7/2020 |
| WO | 2021/207691 | A1 | 10/2021 |
| WO | 2022/182483 | A1 | 9/2022 |

OTHER PUBLICATIONS

Extended European Search Report issued in EP Patent Application No. 21750642.7, Jun. 11, 2024.
Sato K. et al., "Photoinduced Ligand Release from a Silicon Phthalocyanine Dye Conjugated with Monoclonal Antibodies: A Mechanism of Cancer Cell Cytotoxicity after Near-Infrared Photoimmunotherapy", ACS Cent Sch. Nov. 2, 20188; 4(11):1559-1569. Doi: 10.1021/acscentsci.8b00565. Epub Nov. 6, 2018. PMID: 30555909; PMCID: PMC6276043. (Year: 2018).
Office Action issued in U.S. Appl. No. 17/237,709, filed Feb. 14, 2023.
Li et al., "Size-Tunable Targeting-Triggered Nanophotosensitizers Based on Self-Assembly of a Phthalocyanine- Biotin Conjugate for Photodynamic Therapy", ACS Appl Mater Interfaces, Oct. 9, 2019; 11(40):36435-36443.
DeGuire et al., "Fluorescent Probes of the Apoptolidins and their Utility in Cellular Localization Studies", Angew Chem Int Ed Engl., Jan. 1, 20152; 54(3):961-4.
Office Action issued in Japanese Patent Application No. 2019-179281, Oct. 17, 2023, translation.
JSMI Report, 2016, vol. 10, No. 1, pp. 43-45; discussed in JP OA.
Takahashi et al., Pharmaceutical Society of Japan, 2019, vol. 32, No. 9, p. 210 23PO-am 103; discussed in JP OA.
Pratesi et al., "Design and solid phase synthesis of new DOTA conjugated (+)-biotin dimers planned to develop molecular weight-tuned avidin oligomers", Organic & Biomolecular Chemistry, 2015, vol. 13, pp. 3988-4001.
Zheng, B. et al., "Synthesis and photodynamic activities of integrin-targetingsilicon (IV) phthalocyanine-cRGD conjugates", European Journal of Medicinal Chemistry, vol. 155, 2018, pp. 24-33.
Galstyan, A et al., "Labeling and Selective Inactivation of Grarr-Positive Bacteria Employing Bimodal Photoprobes with Dual Readouts", Chern. Eur. J., vol. 22, 2016, pp. 5243-5252.
Lin, K. et al., "Combination of Optical and Electrical Loss Analyses for a Si-Phthalocyanine Dye-Sensitized Solar Cell", J. Phys. Chem. B, vol. 118, 2014, pp. 14027-14036.
Mitsunaga et al. "Nature Medicine" 2011, 17, 16855.
ISR/WO issued in International Patent Application No. PCT/JP2021/004100, Apr. 13, 2021, translation.
IPRP issued in International Patent Application No. PCT/JP2021/004100, Jul. 28, 2022, translation.
Office Action issued in Chinese Patent Application No. 202180013061.X, Dec. 15, 2023, translation.
Office Action issued in CN Patent Application No. 202180013061.X, dated Aug. 24, 2024, translation.
Office Action issued in Japanese Patent Application No. 2021-575859, 24 Dec. 24, 2024, Translation.
Decision on Rejection issued in CN Patent Application No. 202180013061.X, Nov. 6, 2024, translation.
Office Action issued in U.S. Appl. No. 17/237,709, filed Jul. 24, 2023.
Office Action issued in Japanese Patent Application No. 2019-179281. Mar. 26, 2024, translation.
Ke Li et al., Journal of Photochemistry & Photobiology, 2019, B:Biology 190, pp. 1-7.

* cited by examiner

[Fig. 1]
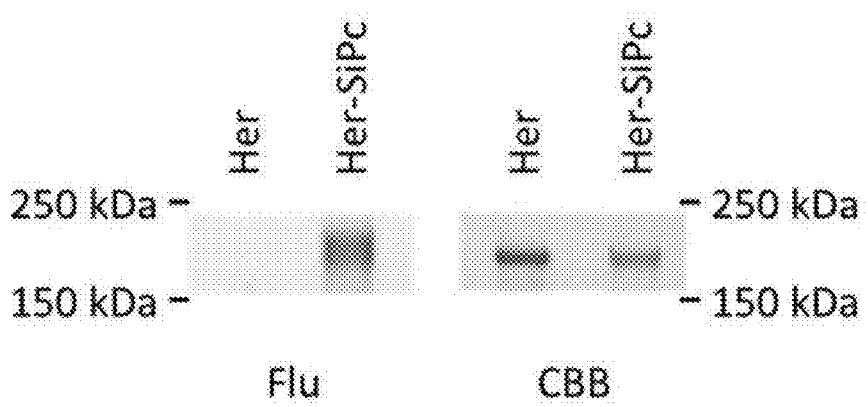
[Fig. 2]
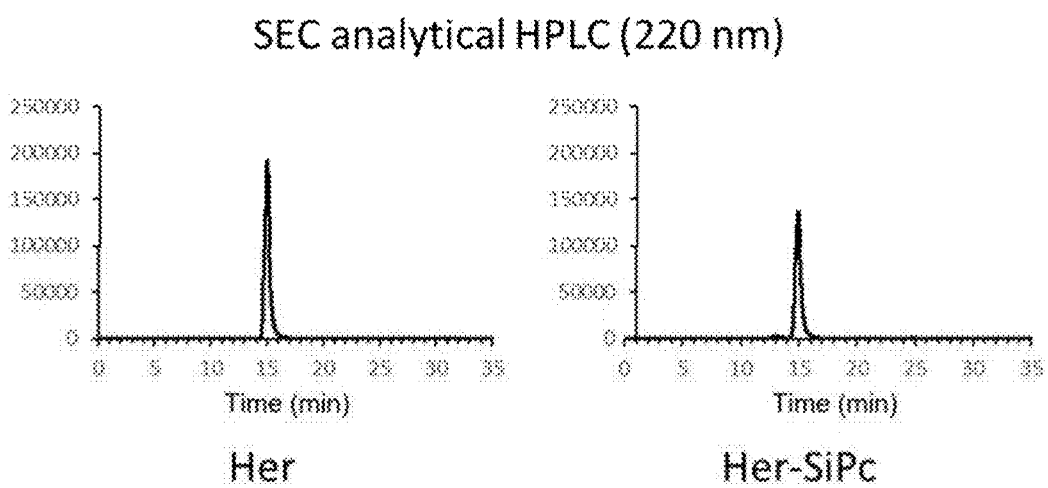

[Fig. 3]
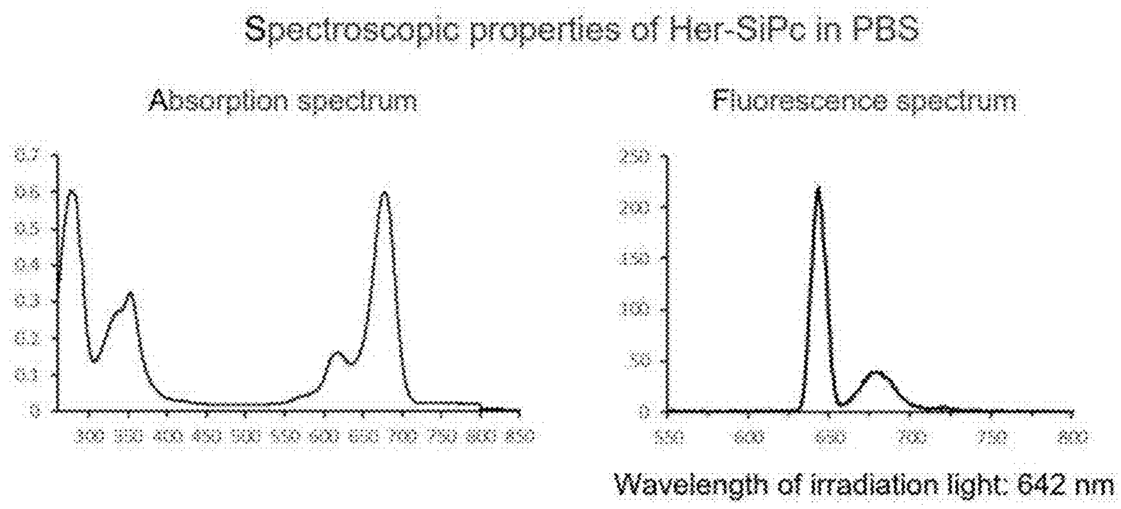
[Fig. 4]
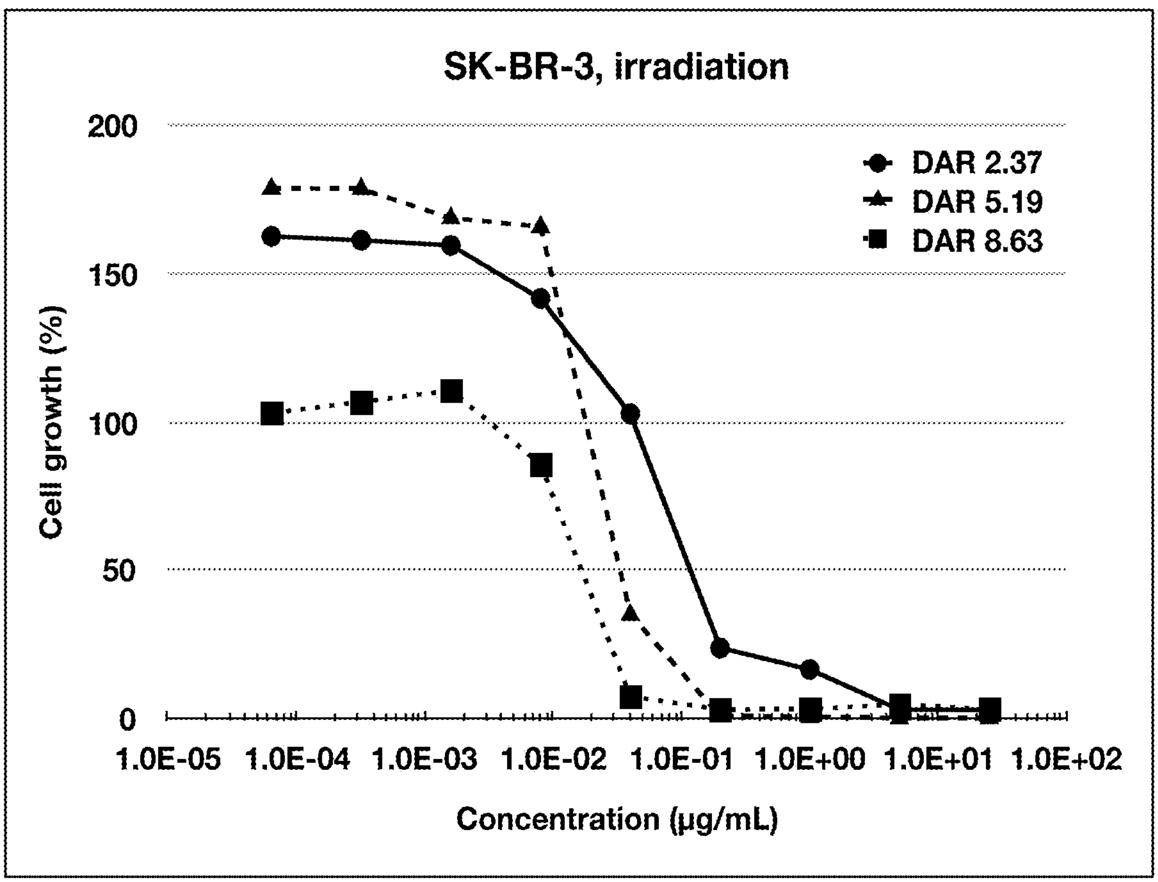

[Fig. 5]
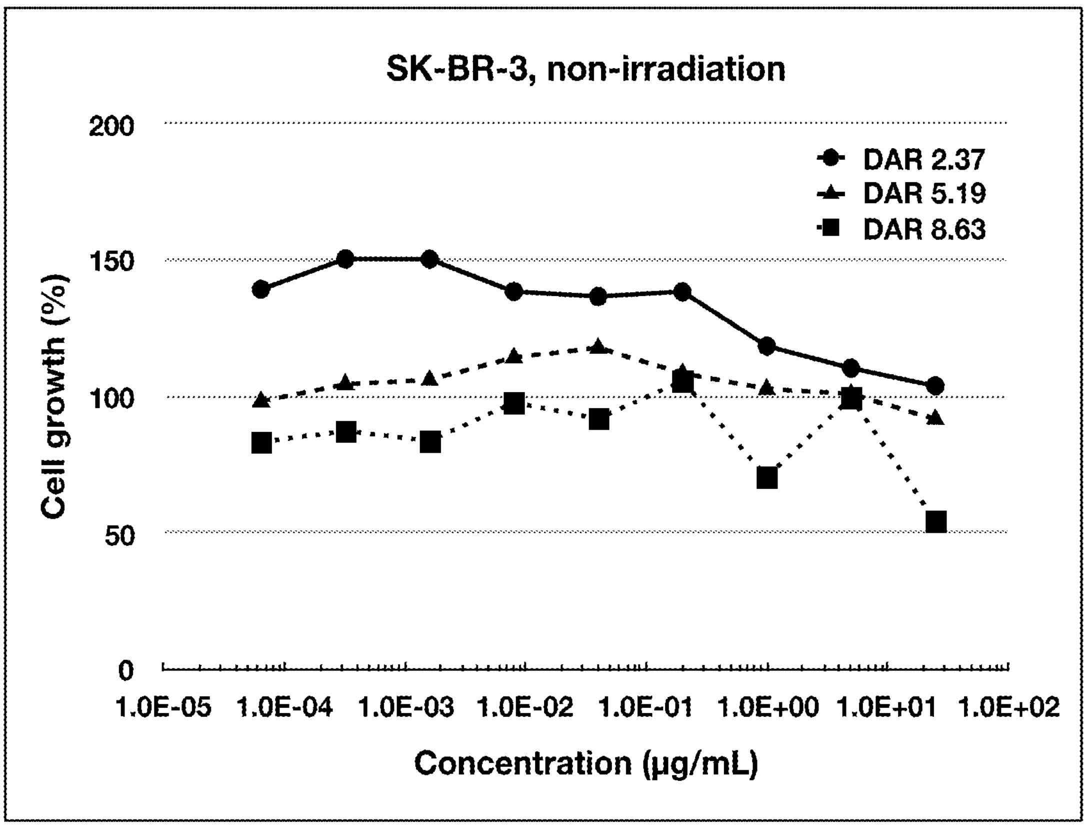

[Fig. 6]
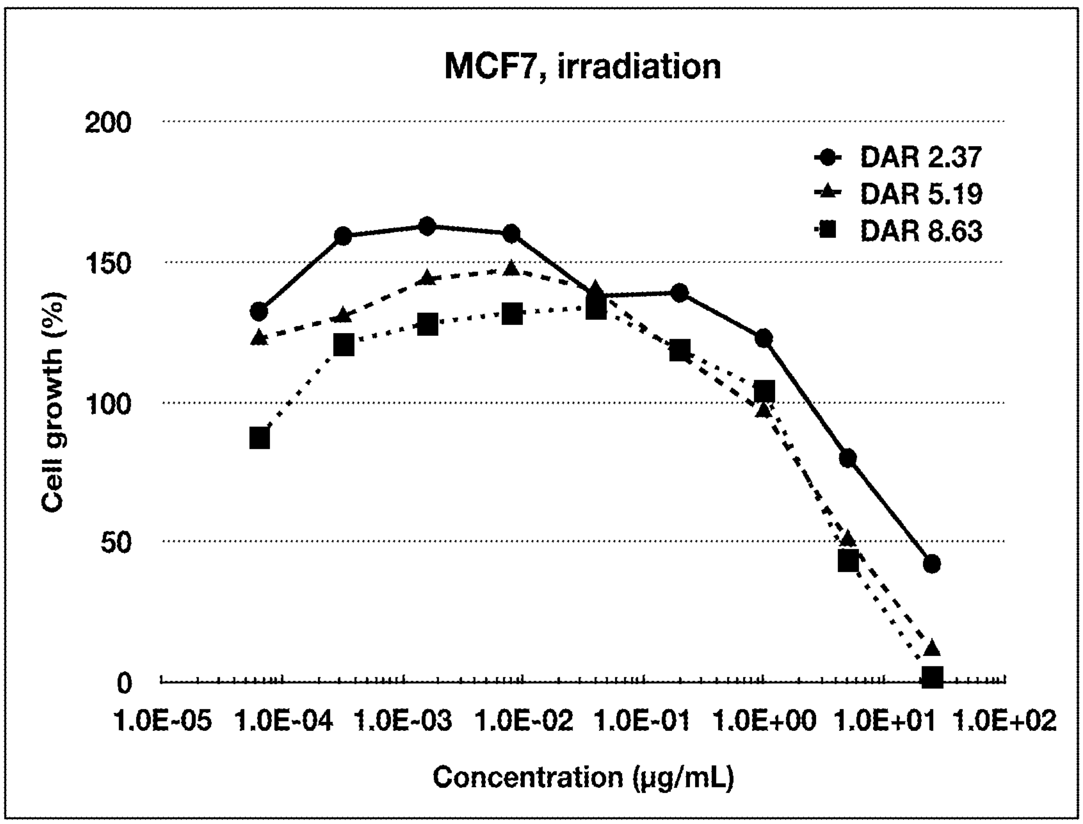

[Fig. 7]
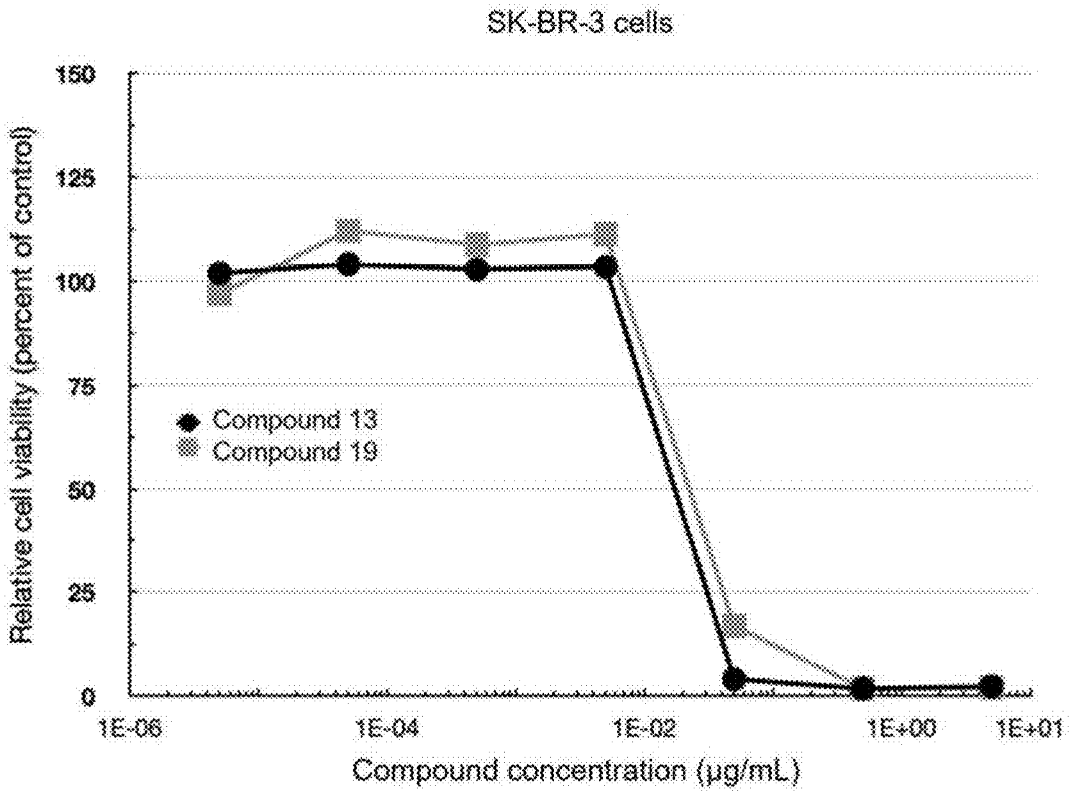

[Fig. 8]
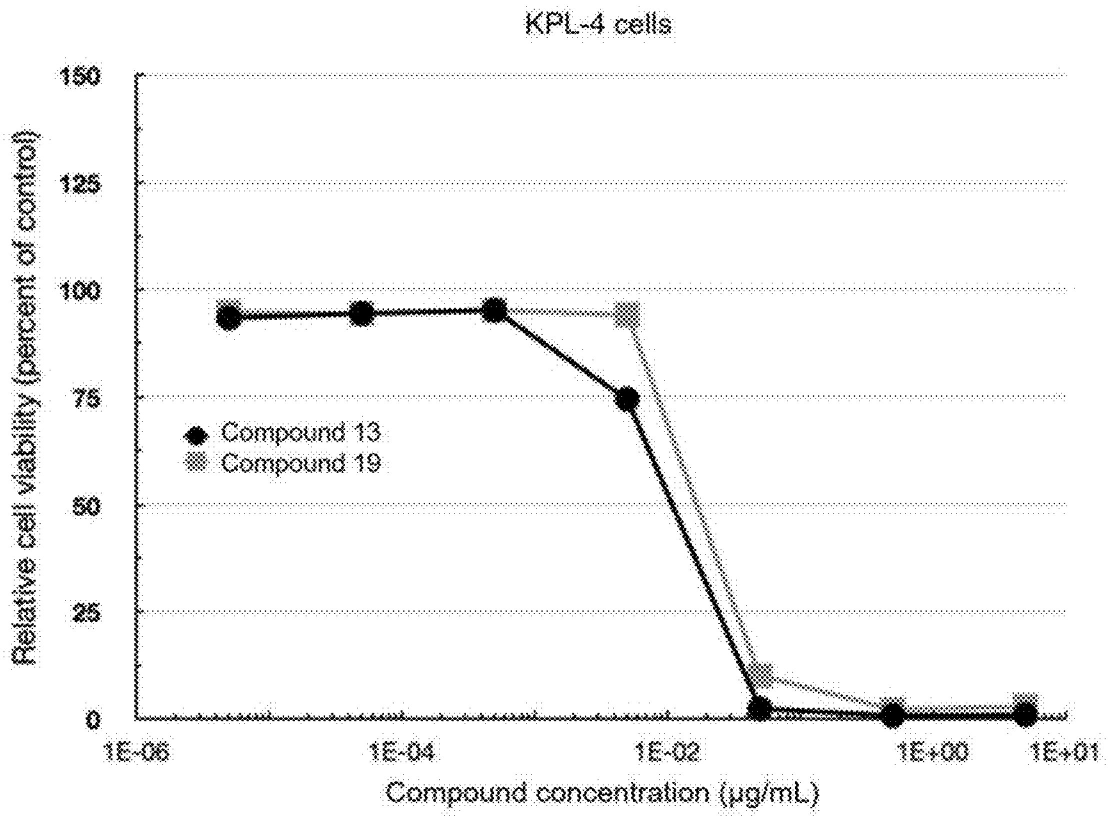

CONJUGATE OF PHTHALOCY ANINE DYE AND ANTIBODY OR PEPTIDE

TECHNICAL FIELD

The present invention relates to a phthalocyanine dye, a conjugate of a phthalocyanine dye and an antibody or a peptide, and a method for producing them.

BACKGROUND ART

Photoimmunotherapy is a therapeutic method of using a photosensitizer and an irradiation light to destroy specific cells in a body. When a photosensitizer is exposed to alight with a specific wavelength, it generates cytotoxic reactive oxygen species capable of inducing apoptosis, necrosis, and/or autophagy to around cells. For example, Patent Document 1 discloses a method of killing cells, comprising: a step of allowing cells comprising a cell surface protein to come into contact with a therapeutically effective amount of one or more antibody-IR700 molecules, wherein the antibody specifically binds to the cell surface protein; a step of irradiating the cells with alight at a wavelength of 660 to 740 nm and at a dose of at least 1 $Jcm^{-2}$; and a step of allowing the cells to come into contact with one or more therapeutic agents at approximately 0 to 8 hours after the irradiation, thereby killing the cells. Patent Document 2 discloses a method of inducing cytotoxicity to a subject affected with a disease or a pathology, comprising: (a) administering to a subject, a therapeutically effective drug comprising a phthalocyanine dye such as IRDye (registered trademark) 700DX conjugated with a probe specifically binding to the cell of the subject; and (b) irradiating the cell with an appropriate excitation light in an amount effective for inducing cell death.

PRIOR ART DOCUMENTS

Patent Documents

Patent Document 1: Japanese Patent No. 6127045
Patent Document 2: JP Patent Publication (Kohyo) No. 2017-524659 A

SUMMARY OF INVENTION

Objects to be Solved by the Invention

It is an object of the present invention to provide a novel phthalocyanine dye for use in photoimmunotherapy and a method for producing the same. It is another object of the present invention to provide a conjugate of the above-described phthalocyanine dye and an antibody or a peptide. It is a further object of the present invention to provide a therapeutic agent comprising the above-described conjugate.

Means for Solving the Objects

As a result of intensive studies directed towards achieving the above-described objects, the present inventor has found that the growth of cancer cells can be suppressed by photoimmunotherapy using a conjugate of a phthalocyanine dye and an antibody, thereby completing the present invention.

Specifically, according to the present invention, the following inventions are provided.

<1> A compound represented by the following formula (1) or a salt thereof.

[Formula 1]

(1)

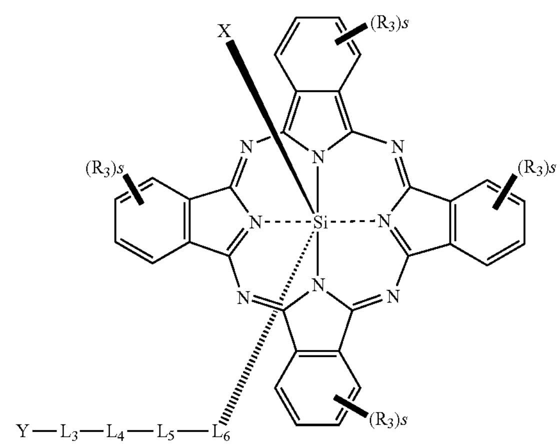

wherein

X represents a substituent having a hydrophilic group at the terminus thereof, $L_3$, $L_4$, $L_5$, and $L_6$ each independently represent a divalent linking group, Y represents a group capable of binding to an antibody or a peptide, $R_3$ represents an alkyl group containing 1 to 6 carbon atoms, an alkoxy group containing 1 to 6 carbon atoms, a halogen atom, $—SR_{11}$, $—SOR_{12}$, an aryl group containing 6 to 10 carbon atoms, $—N(R_{13})(R_{14})$, or $—NO_2$, or two adjacent $R_3$s may together form an aryl group containing 6 to 10 carbon atoms, $R_{11}$, $R_{12}$, $R_{13}$, and $R_{14}$ each independently represent an alkyl group containing 1 to 6 carbon atoms or an alkoxy group containing 1 to 6 carbon atoms, wherein the aryl group may be optionally substituted with an alkyl group containing 1 to 6 carbon atoms or an alkoxy group containing 1 to 6 carbon atoms, and wherein the alkyl group and the alkoxy group may be optionally substituted with a halogen atom, and when a plurality of $R_3$s are present, the plurality of $R_3$s may be identical to or different from one another, and s represents an integer of 0 to 4.

<2> The compound or a salt thereof according to <1>, wherein X represents a substituent having a sulfonic acid group at the terminus thereof.

<3> The compound or a salt thereof according to <1> or <2>, wherein X represents:

[Formula 2]

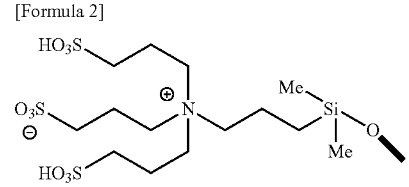

<4> The compound or a salt thereof according to any one of <1> to <3>, wherein Y represents an active ester of a carboxyl group.

<5> The compound or a salt thereof according to any one of <1> to <4>, wherein $L_3$ represents:

[Formula 3]

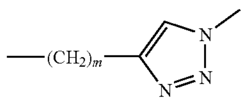

wherein m represents an integer of 1 to 5.

<6> The compound or a salt thereof according to any one of <1> to <5>, wherein $L_4$ represents $—[(CH_2)_p—O)]_q—$ (wherein p and q each independently represent an integer of 1 to 5), or $—(CH_2)_r—$ wherein r represents an integer of 1 to 5.

<7> The compound or a salt thereof according to any one of <1> to <6>, wherein $L_5$ represents —CONH—, —NHCO—, —COO—, —OCO—, —CO-$(Xaa)_s$-NH—, or —NH-$(Xaa)_t$-CO— wherein s and t represent an integer of 1 to 10, and Xaa represents an amino acid residue having a hydrophilic group at the terminus of a side chain thereof.

<8> The compound or a salt thereof according to any one of <1> to <7>, wherein $L_6$ represents $—(CH_2)—Si(R^1)(R^2)—O—$ wherein r represents an integer of 1 to 5, and $R^1$ and $R^2$ each independently represent an alkyl group containing 1 to 4 carbon atoms.

<9> Any of the following compounds:

[Formula 4]

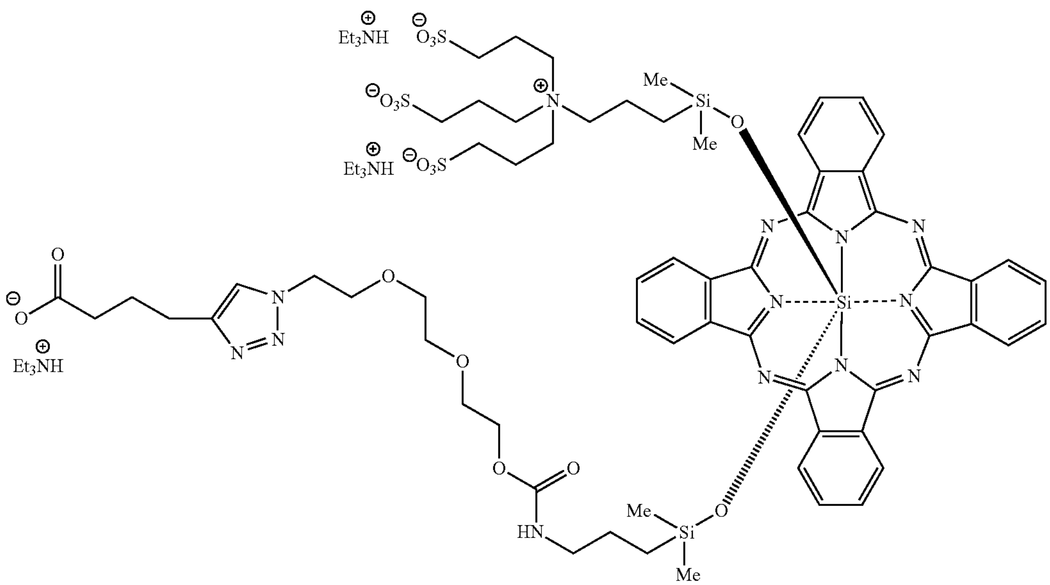

[Formula 5]

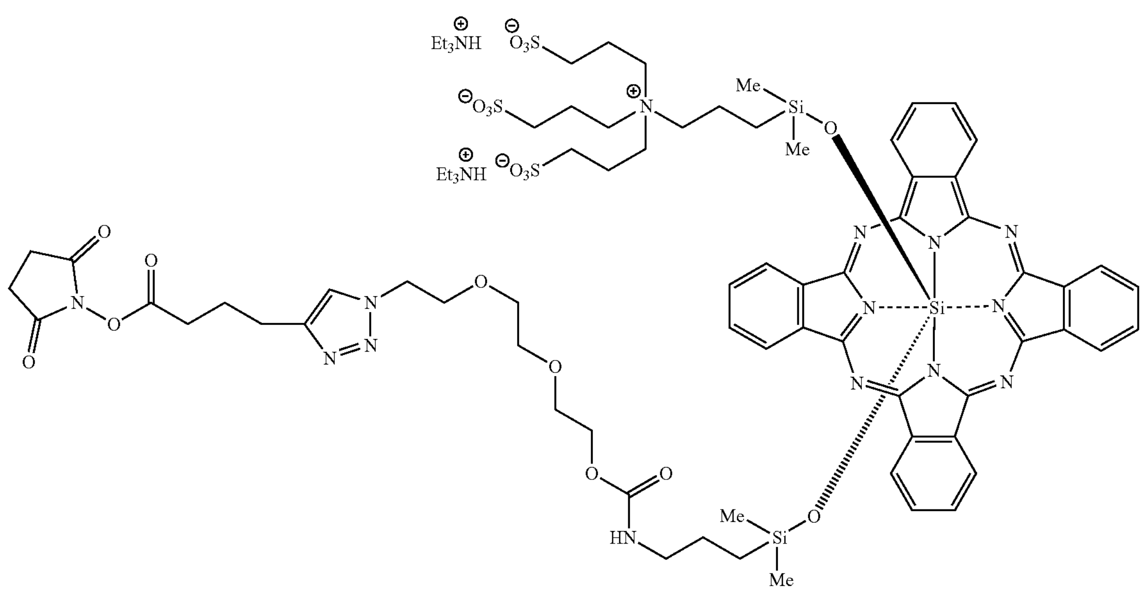

-continued
[Formula 6]
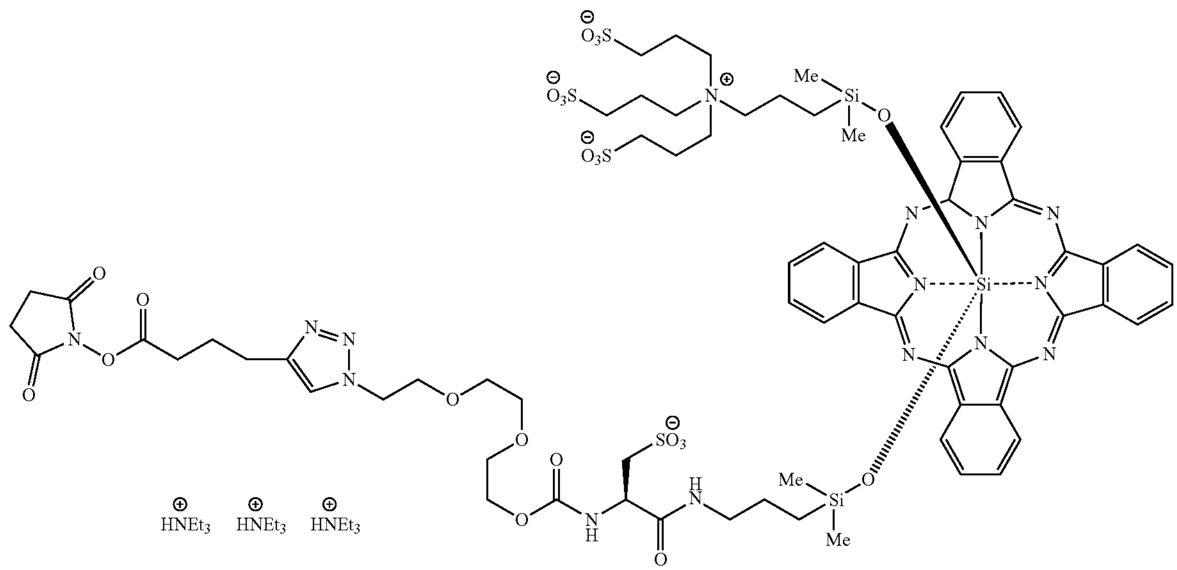
[Formula 7]
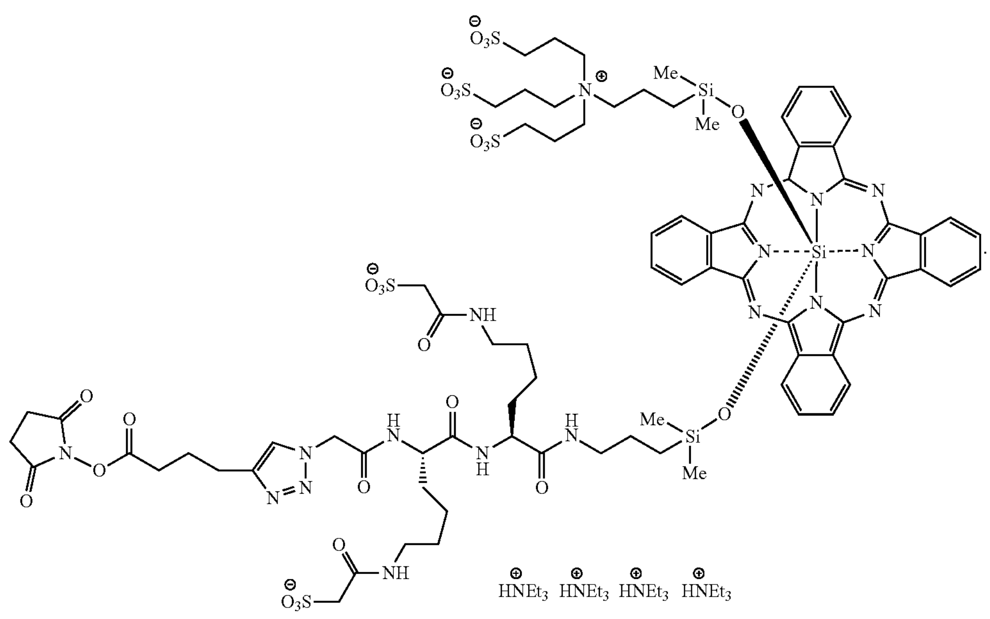

<10> A conjugate formed by binding an antibody or a peptide to a group represented by Y in the compound or a salt thereof according to any one of <1> to <8>.

<11> The conjugate according to <10>, wherein the antibody is an anti-HER2 antibody.

<12> The conjugate according to <10> or <11>, wherein 1 to 7 molecules of the compound or a salt thereof according to any one of claims 1 to 8 bind to 1 molecule of the antibody.

<13> A therapeutic agent comprising the conjugate according to any one of <10> to <12>.

<14>] A method for producing the compound or a salt thereof according to any one of <1> to <9>, comprising the following steps (1) to (5):

(1) a step of reacting the following Compound 1:

[Formula 8]

1

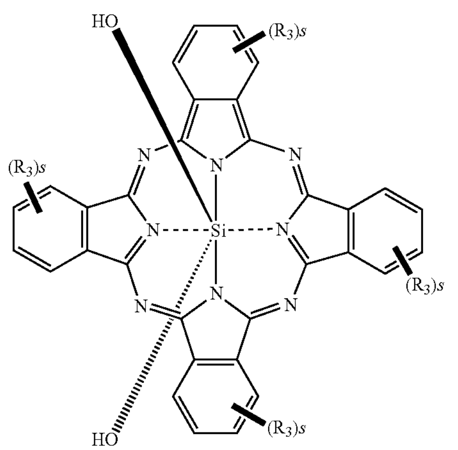

with a compound represented by $L_6$-$NH_2$ to produce the following Compound 2:

[Formula 9]

2

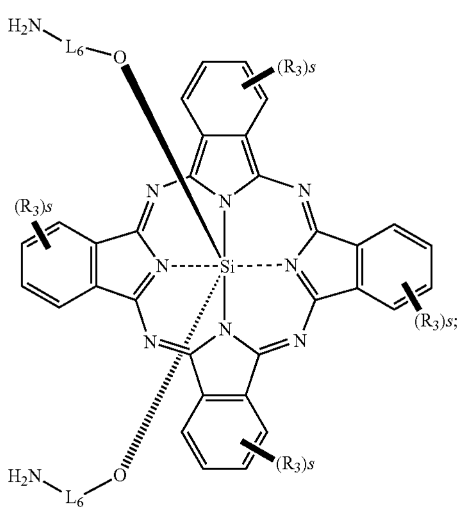

(2) a step of reacting the above Compound 2 with a compound represented by Z1-L4-Z2 wherein Z1 represents an azide group, and Z2 represents an active ester of a carboxyl group, to produce the following Compound 4:

[Formula 10]

4

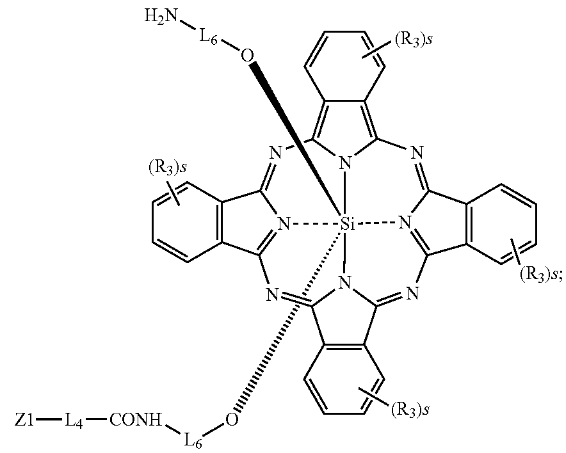

(3) a step of reacting the above Compound 4 with a reagent for introduction of a hydrophilic group to produce the following Compound 5:

[Formula 11]

5

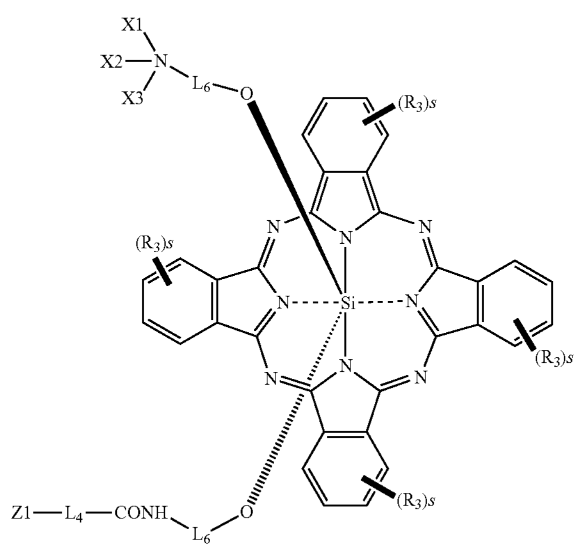

wherein X1, X2, and X3 each represent a group containing a hydrophilic group;

(4) a step of reacting the above Compound 5 with $CH{\equiv}C$—$(CH_2)_t$—COONa wherein t represents an integer of 1 to 5, to produce the following Compound 6 or a salt thereof:

[Formula 12]

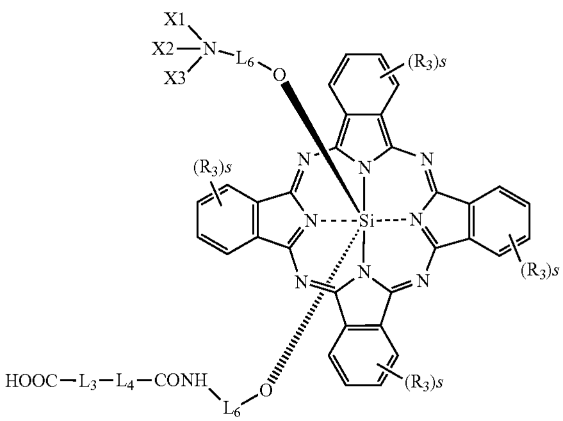

6 wherein $R_3$ represents an alkyl group containing 1 to 6 carbon atoms, an alkoxy group containing 1 to 6 carbon atoms, a halogen atom, —$SR_{11}$, —$SOR_{12}$, an aryl group containing 6 to 10 carbon atoms, —$N(R_{13})(R_{14})$, or —$NO_2$, or two adjacent $R_3$s may together form an aryl group containing 6 to 10 carbon atoms, $R_{11}$, $R_{12}$, $R_{13}$, and $R_{14}$ each independently represent an alkyl group containing 1 to 6 carbon atoms or an alkoxy group containing 1 to 6 carbon atoms, wherein the aryl group may be optionally substituted with an alkyl group containing 1 to 6 carbon atoms or an alkoxy group containing 1 to 6 carbon atoms, and wherein the alkyl group and the alkoxy group may be optionally substituted with a halogen atom, and when a plurality of $R_3$s are present, the plurality of $R_3$s may be identical to or different from one another, and s represents an integer of 0 to 4; and (5) a step of subjecting the carboxyl group that binds to L3 in the above Compound 6 to active esterification.

Advantageous Effects of Invention

The growth of cancer cells can be suppressed by photo-immunotherapy using the conjugate of a phthalocyanine dye and an antibody according to the present invention.

BRIEF DESCRIPTION OF DRAWINGS

FIG. 1 shows the results obtained by analyzing Herceptin and Her-SiPc according to SDS-PAGE.

FIG. 2 shows the results obtained by analyzing Herceptin and Her-SiPc according to size exclusion HPLC under the after-mentioned measurement conditions.

FIG. 3 shows the spectroscopic properties of Her-SiPc in PBS.

FIG. 4 shows the results of an in vitro cytotoxicity test using Her-SiPc (SK-BR-3 cells, with light irradiation).

FIG. 5 shows the results of an in vitro cytotoxicity test using Her-SiPc (SK-BR-3 cells, without light irradiation).

FIG. 6 shows the results of an in vitro cytotoxicity test using Her-SiPc (MCF7 cells, with light irradiation).

FIG. 7 shows the results of an in vitro cytotoxicity test using Her-SiPc (SK-BR-3 cells, with light irradiation).

FIG. 8 shows the results of an in vitro cytotoxicity test using Her-SiPc (KPL-4 cells, with light irradiation).

EMBODIMENT OF CARRYING OUT THE INVENTION

Hereinafter, the present invention will be described in more detail.

(1) Phthalocyanine Dye

The present invention relates to a phthalocyanine dye, and specifically relates to a compound represented by the following formula (1) or a salt thereof:

[Formula 13]

(1)

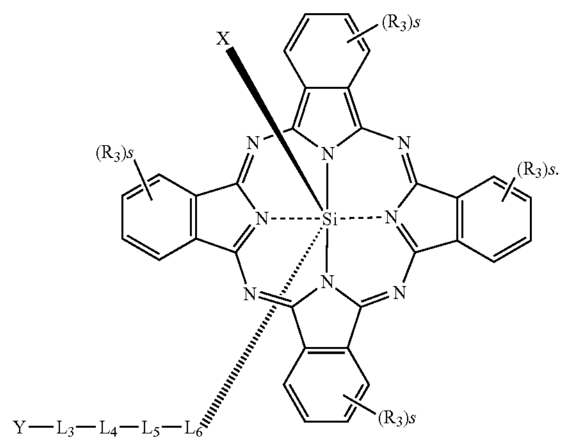

In the above formula (1), X represents a substituent having a hydrophilic group at the terminus thereof. The hydrophilic group is preferably a sulfonic acid group, a phosphoric acid group, an ammonium group, or the like.

X is preferably a substituent having a sulfonic acid group at the terminus thereof.

An example of X may be a group represented by the following formula:

[Formula 14]

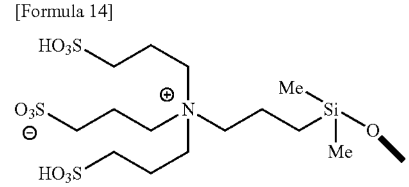

In the present description, Me represents a methyl group.

$L_3$, $L_4$, $L_5$, and $L_6$ each independently represent a divalent linking group.

$L_3$ is preferably the following:

[Formula 15]

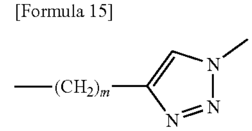

wherein m represents an integer of 1 to 5.

$L_4$ is preferably m-[$(CH_2)_p$—O)]$_q$— (wherein p and q each independently represent an integer of 1 to 5), or —$(CH_2)_r$— (wherein r represents an integer of 1 to 5).

$L_5$ is preferably —CONH—, —NHCO—, —COO—, —OCO—, —CO—$(Xaa)_s$-NH—, or —NH-$(Xaa)_t$-CO— (wherein s and t each represent an integer of 1 to 10, and Xaa represents an amino acid residue having a hydrophilic group at the terminus of a side chain thereof).

$L_5$ is more preferably —CONH—, or —CO-$(Xaa)_s$-NH— (wherein s represents an integer of 1 to 10, and Xaa represents an amino acid residue having a hydrophilic group at the terminus of a side chain thereof). s is more preferably 1 or 2.

The amino acid residue represented by Xaa is preferably a group represented by —NH—CH($R_{10}$)—CO—. Besides, —NH in the amino acid residue forms an amide bond together with —CO— adjacent to the amino acid residue, and CO— in the amino acid residue forms an amide bond together with —NH— adjacent to the amino acid residue. $R_{10}$ represents an amino acid having a hydrophilic group at the terminus of a side chain thereof. The hydrophilic group at the terminus of the side chain of the amino acid represented by $R_{10}$ is preferably a sulfonic acid group, a phosphoric acid group, an ammonium group or the like, and is particularly preferably a sulfonic acid group. Examples of $R_{10}$ may include —$CH_2$—$SO_3$—, and —$(CH_2)_u$—NHCO—$CH_2$—$SO_3^-$ (wherein u represents an integer of 1 to 10, and preferably represents an integer of 2 to 6).

$L_6$ is preferably —$(CH_2)_r$—, —$(CH_2)_r$—O—, or —$(CH_2)_r$—Si($R^1$)($R^2$)—O— (wherein r represents an integer of 1 to 5, and $R^1$ and $R^2$ each independently represent an alkyl group containing 1 to 4 carbon atoms). $R^1$ and $R^2$ are particularly preferably methyl groups.

Y represents a group capable of binding to an antibody or a peptide. Y is preferably an active ester of a carboxyl group, and is more preferably an succinimidyl ester of a carboxyl group.

$R_3$ represents an alkyl group containing 1 to 6 carbon atoms, an alkoxy group containing 1 to 6 carbon atoms, a halogen atom, —$SR_{11}$, —$SOR_{12}$, an aryl group containing 6 to 10 carbon atoms, —N($R_{13}$)($R_{14}$), or —$NO_2$, or two adjacent $R_3$s may together form an aryl group containing 6 to 10 carbon atoms. $R_{11}$, $R_{12}$, $R_{13}$, and $R_{14}$ each independently represent an alkyl group containing 1 to 6 carbon atoms or an alkoxy group containing 1 to 6 carbon atoms.

Herein, the aryl group may be optionally substituted with an alkyl group containing 1 to 6 carbon atoms or an alkoxy group containing 1 to 6 carbon atoms Herein, the alkyl group and the alkoxy group may be optionally substituted with a halogen atom.

When a plurality of $R_3$s are present, the plurality of $R_3$s may be identical to or different from one another.

s represents an integer of 0 to 4. s is preferably 0.

The halogen atom may be any of fluorine, chlorine, bromine and iodine, and the halogen atom is preferably fluorine, chlorine, or bromine.

The compound of the present invention can be synthesized in accordance with the methods described in Production Examples 1 to 5 in the after-mentioned Examples. That is to say, according to the present invention, a method for producing the compound of the present invention or a salt thereof, comprising the following steps (1) to (5), is provided:

(1) A step of reacting the following Compound 1:

[Formula 16]

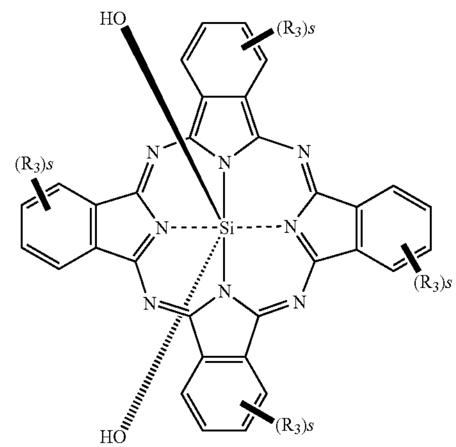

1 with a compound represented by $L_6$-$NH_2$ to produce the following Compound 2:

[Formula 17]

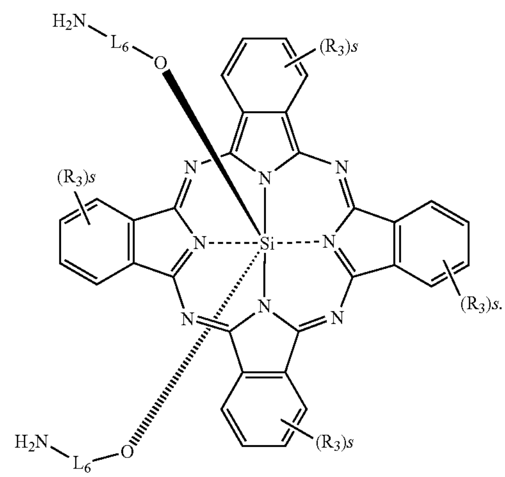

2

The compound represented by $L_6$-$NH_2$ (for example, (3-aminopropyl)dimethylethoxysilane) and dry pyridine are added to Compound 1, and then, the obtained mixture is stirred and is heated to reflux. The solvent is distilled away from the reaction mixture under reduced pressure, and the residue is then purified by column chromatography, so that Compound 2 can be obtained.

(2) A step of reacting the above Compound 2 with a compound represented by ZT-L4-Z2 (wherein Z1 represents an azide group, and Z2 represents an active ester of a carboxyl group) to produce the following Compound 4:

[Formula 18]

4

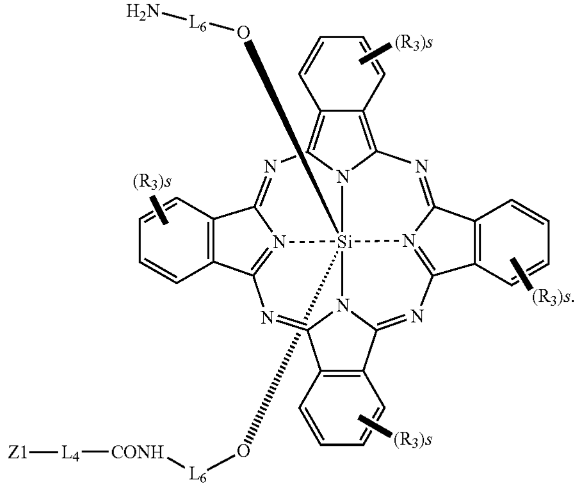

A dry dichloromethane solution, in which Compound 2 is dissolved, is cooled to 0° C., and thereafter, a dry dichloromethane solution of the compound represented by Z1-L4-Z2 (wherein Z1 represents an azide group, and Z2 represents an active ester of a carboxyl group) is added to the above-obtained solution, while stirring. The mixed solution is stirred at room temperature, while shielding the light. The solvent is distilled away from the reaction mixture under reduced pressure, and the residue is then purified by column chromatography, so that Compound 4 can be obtained.

(3) A step of reacting the above Compound 4 with a reagent for introduction of a hydrophilic group to produce the following Compound 5:

[Formula 19]

5

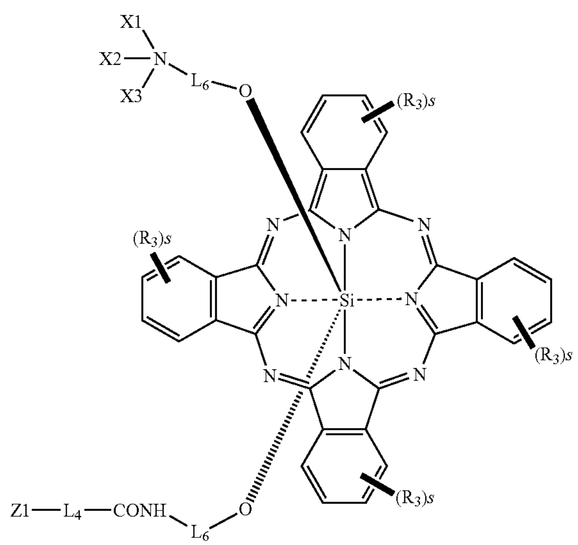

wherein X1, X2, and X3 each represent a group containing a hydrophilic group.

The reagent for introduction of a hydrophilic group (for example, 1,3-propanesultone), diisopropylethylamine, and methanol are added to Compound 4, and the obtained mixture is then stirred, while shielding the light. On Days 7 and 10 after initiation of the reaction, the reagent for introduction of a hydrophilic group (for example, 1,3-propanesultone) and diisopropylethylamine are added to the reaction mixture. On Day 14 after initiation of the reaction, the solvent is distilled away from the reaction mixture under reduced pressure, and the residue diluted with water/acetonitrile (1:1) is then purified by reverse phase HPLC, so that Compound 5 can be obtained.

(4) A step of reacting the above Compound 5 with $CH{\equiv}C{-}(CH_2)_t{-}COONa$ (wherein t represents an integer of 1 to 5) to produce the following Compound 6 or a salt thereof:

[Formula 20]

6

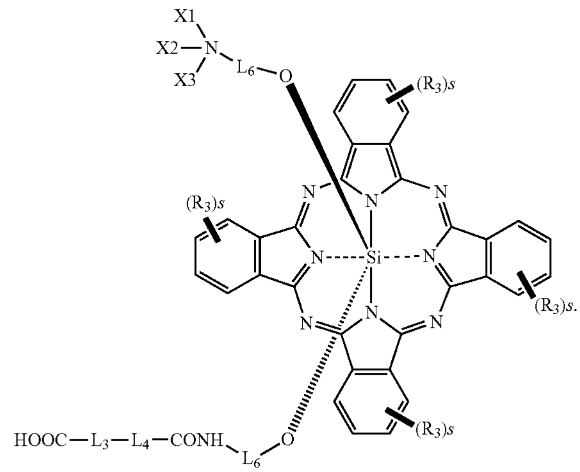

$CH{\equiv}C{-}(CH_2)_t{-}COONa$ (wherein t represents an integer of 1 to 5) (for example, 5-hexynoic acid sodium salt), copper sulfate pentahydrate, tris[(1-benzyl-1H-1,2,3-triazol-4-yl)methyl]amine (0.15 mg, 0.28 μmol), L(+)-ascorbic acid sodium salt, t-butanol, water, and acetonitrile are added to Compound 5, and the obtained mixture is then stirred at room temperature, while shielding the light. The solvent is distilled away from the reaction mixture under reduced pressure, and the residue diluted with water/acetonitrile (1:1) is then purified by reverse phase HPLC, so that Compound 6 can be obtained.

(5) A step of subjecting the carboxyl group that binds to L3 in the above Compound 6 to active esterification.

N,N'-disuccinimidyl carbonate (DSC), triethylamine ($Et_3N$), and dry dimethyl sulfoxide were added to Compound 6, and the obtained mixture is then stirred at room temperature, while shielding the light. A precipitate is generated by adding diethyl ether to the reaction solution. After the removal of a supernatant liquid, the precipitate is washed with diethyl ether, so that a compound of interest can be obtained.

The compound of the present invention can also be synthesized in accordance with the methods described in Production Examples 7 to 11 and Production Examples 13 to 17 in the after-mentioned Examples.

In Production Example 7, a mixed solution of dioxane/water (1:2), in which cysteic acid and $NaHCO_3$ are dissolved, is stirred, and then, a dioxane solution of Compound 3 is slowly added to the mixed solution, followed by stirring the obtained mixture at room temperature. The solvent is distilled away from the reaction mixture under reduced pressure, and the residue diluted with water/acetonitrile (1:1) is then purified by reverse phase HPLC, so that target Compound 8 can be obtained. Production Examples 8 to 11 can be carried out in accordance with Production Examples 2 to 5.

In Production Example 13, Fmoc-Lys(Mmt)-OH, Fmoc-Lys(Mmt)-OH, and azidoacetic acid are successively treated with Wang Resin according to a standard solid phase peptide synthesis method. Thereafter, the reaction mixture is washed with a dichloromethane solution of 1% trifluoroacetic acid/5% triisopropylsilane, and is then washed with dichloromethane. Further, this operation is repeated 19 times. A dimethylformamide solution of sulfoacetic acid, N,N'-diisopropylcarbodiimide, N-hydroxysuccinimide and triethylamine is stirred at room temperature, and is then mixed with the resin. The obtained mixture is reacted at room temperature, and is then washed with dimethylformamide. Further, this operation is repeated twice. The resin is washed with dichloromethane and methanol, and is then dried under reduced pressure. A mixed solution of 95% trifluoroacetic acid/2.5% triisopropylsilane/2.5% water is added to the reaction mixture, and thereafter, the thus obtained mixture is stirred at room temperature and is then filtered. The filtrate is distilled away under reduced pressure, and diethyl ether is then added to the resultant, so as to precipitate a product. After the removal of a supernatant liquid, the residue is dissolved in water and is then purified by reverse phase HPLC, so that target Compound 14 can be obtained. Production Examples 14 to 17 can be carried out in accordance with Production Examples 2 to 5.

(2) Conjugate of phthalocyanine dye and antibody or peptide, and therapeutic agent According to the present invention, a conjugate of the above-described compound of the present invention or a salt thereof, and an antibody or a peptide, is provided. According to the present invention, a therapeutic agent comprising the above-described conjugate is provided.

As an antibody or a peptide, specifically, an antibody or a peptide, which targets the following antigens specifically expressed in cancer, can be used:

Epiregulin (EREG), ROBO 1, 2, 3 and 4, 1-40-β-amyloid, 4-1BB, 5AC, 5T4, ACVR2B, adenocarcinoma antigen, α-fetoprotein, angiopoetin 2, anthrax toxin, AOC3 (VAP-1), B-lymphoma cells, B7-H3, BAFF, β amyloid, C242 antigen, C5, CA-125, carbonic anhydrase 9 (CA-IX), cardiac myosin, CCL11 (eotaxin-1), CCR4, CCR5, CD11, CD18, CD125, CD140a, CD147 (basigin), CD147 (basigin), CD15, CD152, CD154 (CD40L), CD154, CD19, CD2, CD20, CD200, CD22, CD221, CD23 (IgE receptor), CD25 (IL-2 receptor α chain), CD28, CD3, CD30 (TNFRSF8), CD33, CD37, CD38 (cyclic ADP ribose hydrolase), CD4, CD40, CD41 (integrin α-IIb), CD44 v6, CD5, CD51, CD52, CD56, CD6, CD70, CD74, CD79B, CD80, CEA, CFD, ch4D5, CLDN18.2, *Clostridium difficile*, clumping factor A, CSF2, CTLA-4, cytomegalovirus, cytomegalovirus glycoprotein B, DLL4, DR5, *E. coli* Shigatoxin type 1, *E. coli* Shiga toxin type 2, EGFL7, EGFR, endotoxin, EpCAM, episialin, ERBB3, *Escherichia coli*, F protein of respiratory syncytial virus, FAP, fibrin 11 chain, fibronectin extra domain-B, folate receptor 1, Frizzled receptor, GD2, GD3 ganglioside, GMCSF receptor α chain, GPNMB, hepatitis B surface antigen, hepatitis B virus, HER1, HER2/neu, HER3, HGF, HIV-1, HLA-DRβ, HNGF, Hsp90, human β amyloid, human scatter factor receptor kinase, human TNF, ICAM-1 (CD54), IFN-α, IFN-γ, IgE, IgE Fc region, IGF-1 receptor, IGF-I, IgG4, IGHE, IL-1β, IL-12, IL-13, IL-17, IL-17A, IL-22, IL-23, IL-4, IL-5, IL-6, IL-6 receptor, IL-9, ILGF2, influenza A hemagglutinin, insulin-like growth factor I receptor, integrin α4, integrin α4β7, integrin α5β1, integrin α7β7, integrin αIIbβ3, integrin αvβ3, integrin γ induced protein, interferon receptor, interferon α/β receptor, ITGA2, ITGB2 (CD18), KIR2D, L-selectin (CD62L), Lewis-Y antigen, LFA-1 (CD11a), lipoteichoic acid, LOXL2, LTA, MCP-1, mesothelin, MS4A1, MUC1, mucin CanAg, myostatin, N-glycolylneuraminic acid, NARP-1, NCA-90 (granulocyte antigen), NGF, NOGO-A, NRP1, *Oryctolagus cuniculus*, OX-40, oxLDL, PCSK9, PD-1, PDCD1, PDGF-R α, phosphatidylserine, prostate cancer cells, *Pseudomonas aeruginosa*, Rabies virus glycoprotein, RANKL, respiratory syncytial virus, RHD, Rh (Rhesus) factor, RON, RTN4, sclerostin, SDC1, selectin P, SLAMF7, SOST, sphingosine-1-phosphate, TAG-72, TEMI, tenascin C, TFPI, TGFβ1, TGFβ2, TGF-β, TNF-α, TRAIL-R1, TRAIL-R2, tumor antigen CTAA16.88, MUC1 tumor-specific glycosylation, TWEAK receptor, TYRP1 (glycoprotein 75), VEGF-A, VEGFR-1, VEGFR2, vimentin, and VWF.

Among the above-described antigens, epiregulin (EREG), CEA, and HER2 are preferable, and HER2 is particularly preferable.

Various types of molecules can be used as antibodies. Either a polyclonal antibody or a monoclonal antibody maybe used. The subclass of the antibody is not particularly limited. Preferably, IgG, and particularly preferably, $IgG_1$ is used. Furthermore, the term“antibody” includes all of modified antibodies and antibody fragments. Examples of such an antibody include, but are not limited to: a humanized antibody; a human type antibody; a human antibody; antibodies from various types of animals such as a mouse, a rabbit, a rat, a guinea pig and a monkey; a chimeric antibody between a human antibody and an antibody from a different type of animal; diabody; scFv; Fd; Fab; Fab'; and $F(ab)'_2$.

In the conjugate of the present invention, it is preferable that 1 to 7 molecules of the compound of the present invention or a salt thereof bind to one molecule of the antibody.

The phthalocyanine dye can be specifically accumulated in cancer cells by administering the conjugate of the present invention to a patient.

(3) Photoimmunotherapy

The conjugate of the present invention is administered to a subject, and the cells are then irradiated with excitation light in an amount effective for suppression of cell growth or induction of cell death, so that the cell growth can be suppressed or the cell death can be induced, and thereby the subject can be treated.

The subject includes humans and non-human animals. Examples of the subject may include humans and experimental animals such as mice. The subject is preferably affected with a disease regarding which suppression of cell growth or induction of cell death is desired. For example, the subject is affected with cancer or solid tumor.

Examples of cancer may include carcinoma, lymphoma, blastoma, sarcoma, and leukemia or malignant lymphoma. Specific examples of cancer may include squamous cell carcinoma (e.g., epithelial squamous cell carcinoma), lung cancer including small cell lung cancer, non-small cell lung cancer ("NSCLC"), pulmonary adenocarcinoma and pulmonary squamous cell carcinoma, peritoneal cancer, hepatocarcinoma, corpus ventriculi or stomach cancer, including digestive cancer, pancreatic cancer, glioblastoma, cervical cancer, ovarian cancer, liver cancer, bladder cancer, hepatocellular cancer, breast cancer, colon cancer, rectal cancer, colorectal cancer, endometrial membrane cancer or endometrial carcinoma, salivary gland carcinoma, kidney or renal region cancer, prostate cancer, vulvar cancer, thyroid cancer, hepatocellular carcinoma, anal carcinoma, penile carcinoma, and head and neck cancer.

The solid tumor means a benign or malignant, abnormal cell mass that generally does not contain a capsule. Examples of the solid tumor may include glioma, astrocytoma, medulloblastoma, craniopharyngioma, ependymoma, pineal gland tumor, hemangioblastoma, acoustic neuroma, oligodendrocyte, meningioma, melanoma, neuroblastoma, and retinoblastoma.

In the photoimmunotherapy, the conjugate of the present invention is administered to a subject, and thereafter, the subject is irradiated with alight, so that the subject can be treated.

Examples of the administration method to the subject may include, but are not limited to, a local route, an injection (a subcutaneous injection, an intramuscular injection, an intradermal injection, an intraperitoneal injection, an intratumoral injection, an intravenous injection, etc.), an oral route, an ocular route, a sublingual route, a rectal route, a percutaneous route, an intranasal route, a vaginal route, and an inhalation route.

The conjugate of the present invention is preferably administered in a therapeutically effective amount. The therapeutically effective amount per 60 kg is at least 0.5 mg (mg/60 kg), at least 5 mg/60 kg, at least 10 mg/60 kg, at least 20 mg/60 kg, at least 30 mg/60 kg, or at least 50 mg/60 kg. For example, when it is intravenously administered, the applied dose is 1 mg/60 kg, 2 mg/60 kg, 5 mg/60 kg, 20 mg/60 kg, or 50 mg/60 kg, and it is, for example, 0.5 to 50 mg/60 kg. In another example, the therapeutically effective amount is at least 100 μg/kg, at least 500 μg/kg or at least 500 μg/kg, and it is, for example, at least 10 μg/kg. For example, when it is intratumorally or intraperitoneally administered, the dose is 100 μg/kg, 250 μg/kg, approximately 500 μg/kg, 750 μg/kg, or 1000 μg/kg, and it is, for example, 10 μg/kg to 1000 μg/kg. In one example, when it is administered in the form of a solution for local administration, the therapeutically effective amount is 10 μg/ml, 20 μg/ml, 30 μg/ml, 40 μg/ml, 50 μg/ml, 60 μg/ml, 70 μg/ml, 80 μg/ml, 90 μg/ml, 100 μg/ml or the like, or it is 20 μg/ml to 100 μg/ml, or it is at least 500 μg/ml, or at least 1 μg/ml.

The above-described dose can be administered once or divided doses over several administrations (2, 3, or 4 times, etc.), or as a single preparation.

The present conjugate can be administered alone, or can also be administered in the presence of a pharmaceutically acceptable carrier, or can also be administered in the presence of other therapeutic agents (other anticancer agents, etc.).

The present conjugate can bind to target cells or target tissues, such as circulating tumor cells or solid tumor cells. Thereafter, the target cells or tissues are irradiated with alight, so that the above-described conjugate or complex can absorb the light and can damage or destroy the target cells or tissues.

In the photoimmunotherapy, the wavelength of the irradiation light is preferably 660 to 740 nm, and the irradiation light has a wavelength of, for example, 660 nm, 670 nm, 680 nm, 690 nm, 700 nm, 710 nm, 720 nm, 730 nm, or 740 nm. Light irradiation may be carried out using a device equipped with a near infrared (NIR) light emitting diode.

The light irradiation dose is at least 1 J/cm$^2$, for example, at least 4 J/cm$^2$, at least 10 J/cm$^2$, at least 15 J/cm$^2$, at least 20 J/cm$^2$, at least 50 J/cm$^2$, or at least 100 J/cm$^2$. It is, for example, 1 to 500 J/cm$^2$. Light irradiation may be carried out several times (e.g., 2, 3, 4, 5, 6, 7, 8, 9, or 10 times).

The present invention will be more specifically described in the following examples. However, these examples are not intended to limit the scope of the present invention.

EXAMPLES

Production Example 1: Synthesis of Compound 2

[Formula 21]

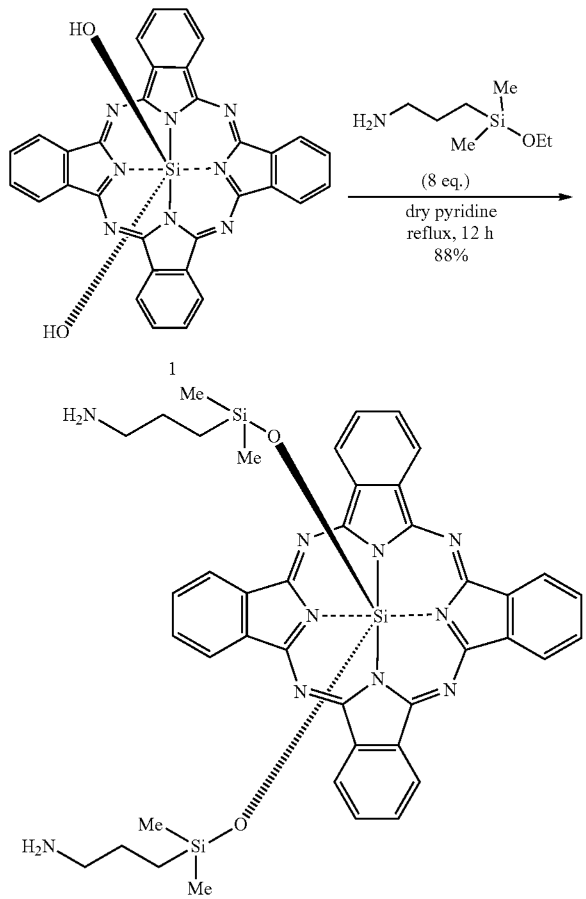

1

2

(3-Aminopropyl)dimethylethoxysilane (113 mg, 700 μmol) and dry pyridine (30 mL) were added to Silicon phthalocyanine dihydroxide 1 (50 mg, 87 μmol), and the obtained mixture was stirred and heated to reflux for 5 hours. Thereafter, the solvent was distilled away from the reaction mixture under reduced pressure, and the residue was then purified by column chromatography (gradient: 1% for 3 min; 1-10% for 15 min; 10-20% for 10 min $CH_3OH$ in $CH_2Cl_2$, Yamazen Corporation Universal™ Column Amino 40 μm 60 Å 2.3×12.3 cm, 16 g, flow rate=10 mL/min) to obtain target Compound 2 (62 mg, 77 μmol, 88%, dark blue).

$^1$H NMR (500 MHz, $CDCl_3$): δ 9.65 (dd, J=2.8 Hz, 5.7 Hz, 8H), 8.34 (dd, J=2.8 Hz, 5.7 Hz, 8H), 1.18 (t, J=7.6 Hz, 4H), −1.23 (m, 4H), −2.30 (m, 4H), −2.86 (s, 12H).

LRMS (ESI): m/z 805.30 [M+H]$^+$

Production Example 2: Synthesis of Compound 4

[Formula 22]

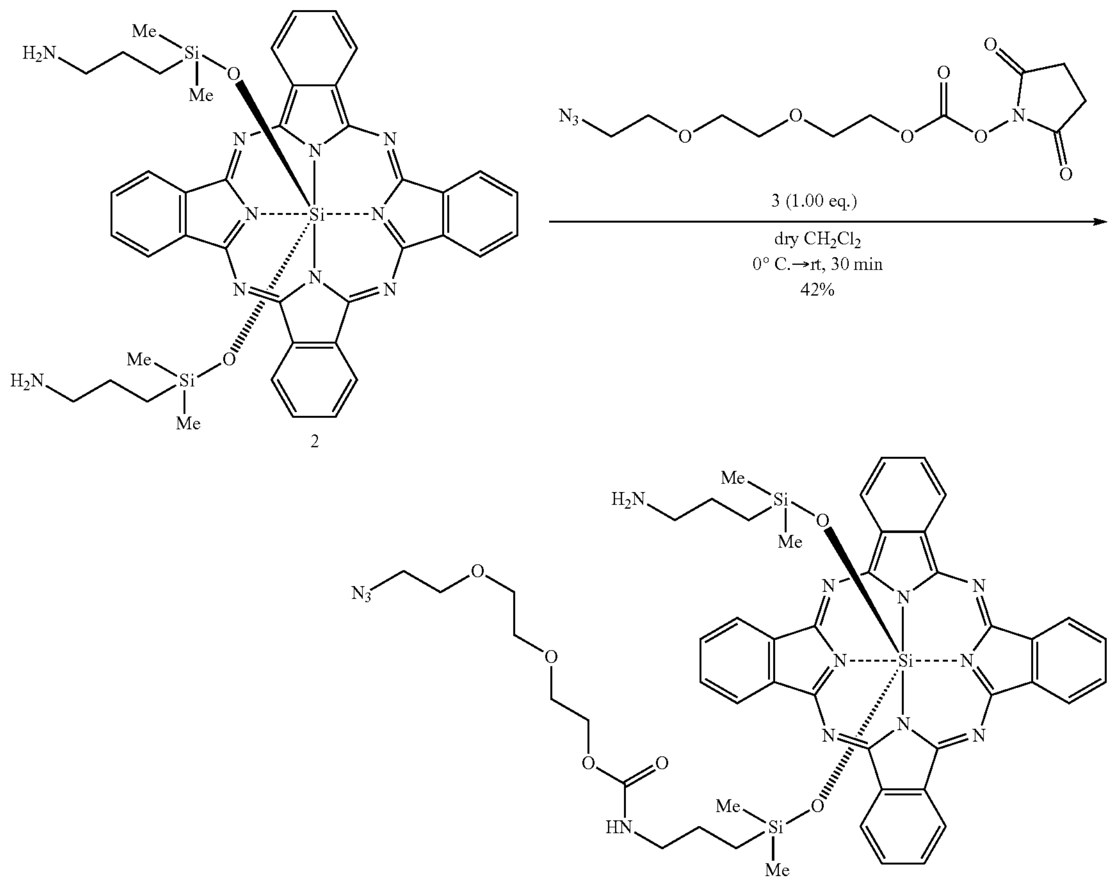

2

4

A dry dichloromethane (27 mL) solution, in which Compound 2 (100 mg, 124 μmol) was dissolved, was cooled to 0° C. Thereafter, a dry dichloromethane (3 mL) solution of Compound 3 (39.2 mg, 124 μmol) was slowly added to the obtained solution, while stirring, and the obtained mixture was then stirred at room temperature for 30 minutes, while shielding the light with an aluminum foil. Thereafter, the solvent was distilled away from the reaction mixture under reduced pressure, and the residue was then purified by column chromatography (gradient: 1% for 3 min; 1-5% for 15 min $CH_3OH$ in $CH_2Cl_2$, Yamazen Corporation Universal™ Column Amino 40 μm 60 Å 2.3×12.3 cm, 16 g, flow rate=10 mL/min) to obtain target Compound 4 (52.3 mg, 51.9 μmol, 42%, dark blue).

$^1H$ NMR (500 MHz, $CDCl_3$): δ 9.65 (dd, J=2.8 Hz, 5.7 Hz, 8H), 8.35 (d, J=2.8 Hz, 5.7 Hz, 8H), 4.08 (t, J=4.8 Hz, 2H), 3.73-3.60 (m, 8H), 3.39 (t, J=5.7 Hz, 2H), 1.76 (m, 2H), 1.18 (t, J=6.7 Hz, 2H), −1.23 (m, 4H), −2.30 (m, 4H), −2.86 (s, 12H).

LRMS (ESI): m/z 1006.85 [M+H]+

Production Example 3: Synthesis of Compound 5

[Formula 23]

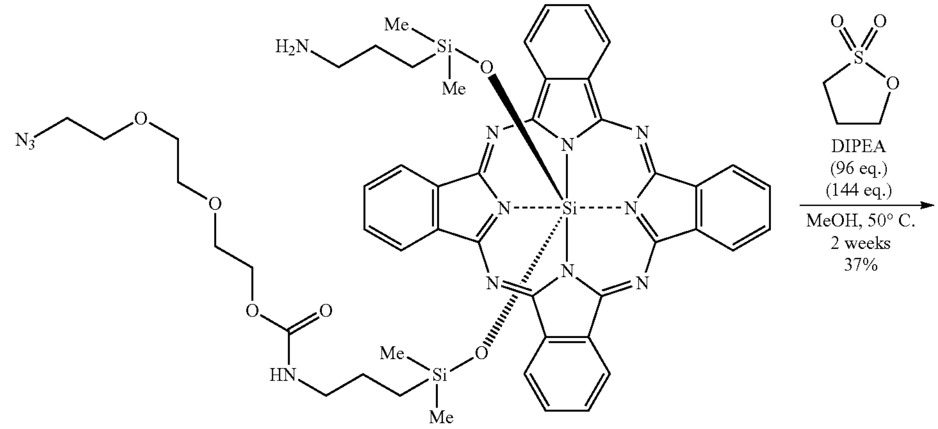

4

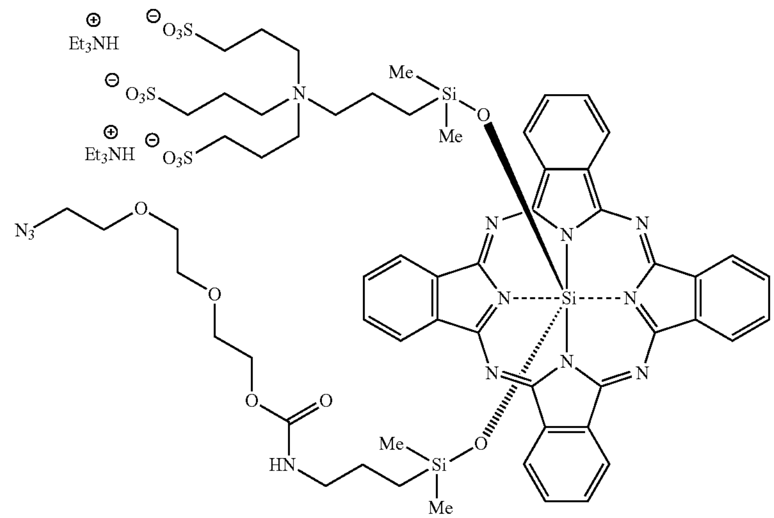

5

1,3-Propanesultone (86.2 mg, 707 μmol), diisopropylethylamine (DIPEA, 137 mg, 1.06 mmol), and methanol (3 mL) were added to Compound 4 (22.2 mg, 22.1 μmol), and the obtained mixture was then stirred at 50° C., while shielding the light with an aluminum foil. On Days 7 and 10 after initiation of the reaction, 1,3-propanesultone (86.2 mg, 707 μmol) and DIPEA (137 mg, 1.06 mmol) were added to the reaction mixture. On Day 14 after initiation of the reaction, the solvent was distilled away from the reaction mixture under reduced pressure, and the residue diluted with water/acetonitrile (1:1) to 6000 μL was divided into two aliquots, which were then purified by reverse phase HPLC (gradient: 50% for 5 min; 50-80% for 25 min; 80-100% for 10 min $CH_3CN$ in 50 mM triethylammonium acetate aqueous solution (pH 7.0), retention time=15.8 min, YMC-Actus Triart C18, flow rate=10 mL/min), so as to obtain target Compound 5 (12.7 mg, 8.09 μmol, 37%, dark blue).

Compound 5: $^1H$ NMR (500 MHz, $CD_3OD$): δ 9.72 (dd, J=2.8 Hz, 5.7 Hz, 8H), 8.46 (dd, J=2.8 Hz, 5.7 Hz, 8H), 3.97 (t, J=4.8 Hz, 2H), 3.63-3.58 (m, 8H), 3.32 (m, 2H), 2.80-2.70 (m, 12H), 1.99 (t, J=6.7 Hz, 2H), 1.70 (m, 6H), 1.60 (t J=6.7 Hz, 2H), −1.07 (m, 2H), −1.14 (m, 2H), −2.12 (m, 2H), −2.28 (m, 2H), −2.82 (s, 6H), −2.89 (s, 6H).

LRMS (ESI): m/z 1372.55 $[M+H]^+$

Production Example 4: Synthesis of Compound 6

[Formula 24]

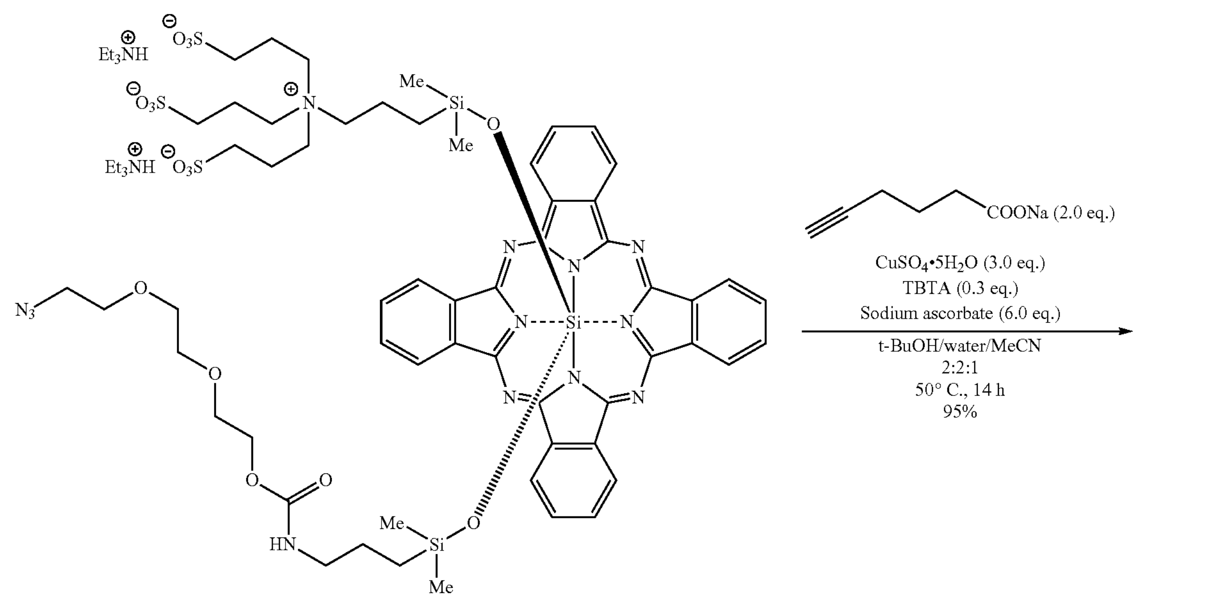

5

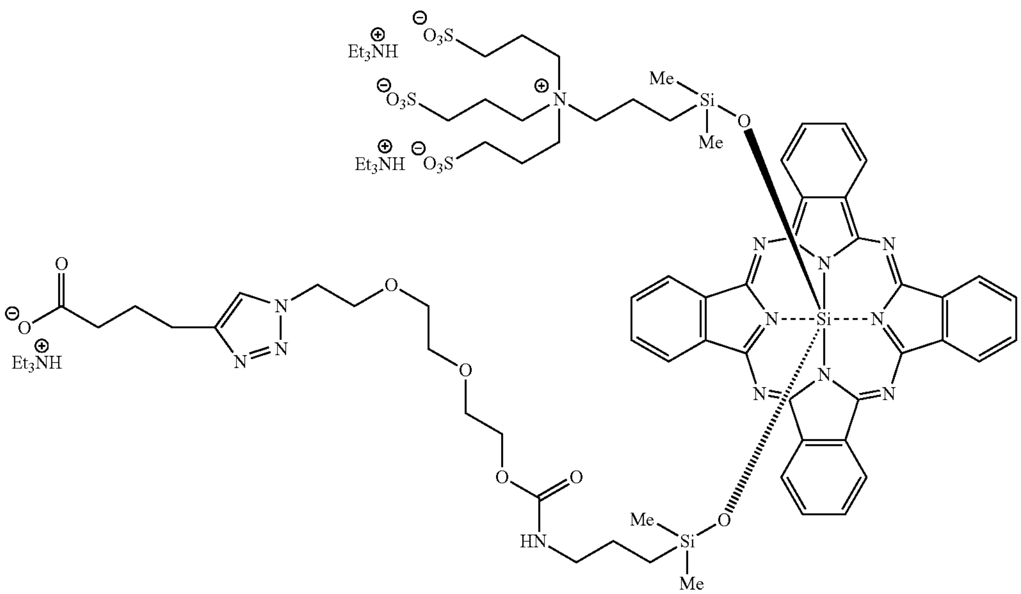

6

5-Hexynoic acid sodium salt (0.19 mg, 1.4 μmol), copper sulfate pentahydrate (0.71 mg, 2.8 μmol), tris[(1-benzyl-1H-1,2,3-triazol-4-yl)methyl]amine (0.15 mg, 0.28 μmol), L(+)-ascorbic acid sodium salt (1.1 mg, 5.7 μmol), t-butanol (300 μL), water (300 μL), and acetonitrile (150 μL) were added to Compound 5 (1.3 mg, 0.95 μmol), and the obtained mixture was then stirred at room temperature for 14 hours, while shielding the light with an aluminum foil. Thereafter, the solvent was distilled away from the reaction mixture under reduced pressure, and the residue diluted with water/acetonitrile (1:1) to 3000 μL was then purified by reverse phase HPLC (gradient: 30% for 5 min; 30-80% for 40 min; 80-100 for 10 min $CH_3CN$ in 50 mM triethylammonium acetate aqueous solution (pH 7.0), retention time=24.6 min, YMC-Triart C18, flow rate=3.5 μL/min) to obtain target Compound 6 (1.6 mg, 0.90 μmol, 95%, dark blue).

$^1H$ NMR (500 MHz, $CD_3OD$): δ 9.73 (dd, J=2.8 Hz, 5.7 Hz, 8H), 8.46 (dd, J=2.8 Hz, 5.7 Hz, 8H), 7.75 (s, 1H), 4.48 (t, J=4.8 Hz, 2H), 3.95 (t, J=3.8 Hz, 2H), 3.83 (t, J=4.8 Hz, 2H), 3.60-3.50 (m, 6H), 2.80-2.70 (m, 12H), 2.67 (t, J=7.6 Hz, 2H), 2.24 (brt, 2H), 2.00 (t, J=8.6 Hz, 2H), 1.90 (t, J=7.6 Hz, 2H), 1.71 (quin, J=7.6 Hz, 6H), 1.61 (t J=6.7 Hz, 2H), −1.03 (brt, 2H), −1.11 (brt, 2H), −2.13 (t, J=8.6 Hz, 2H), −2.27 (t, J=8.6 Hz, 2H), −2.80 (s, 6H), −2.88 (s, 6H).

LRMS (ESI): m/z 1485.15 $[M+H]^+$

Production Example 5: Synthesis of Compound 7

[Formula 25]

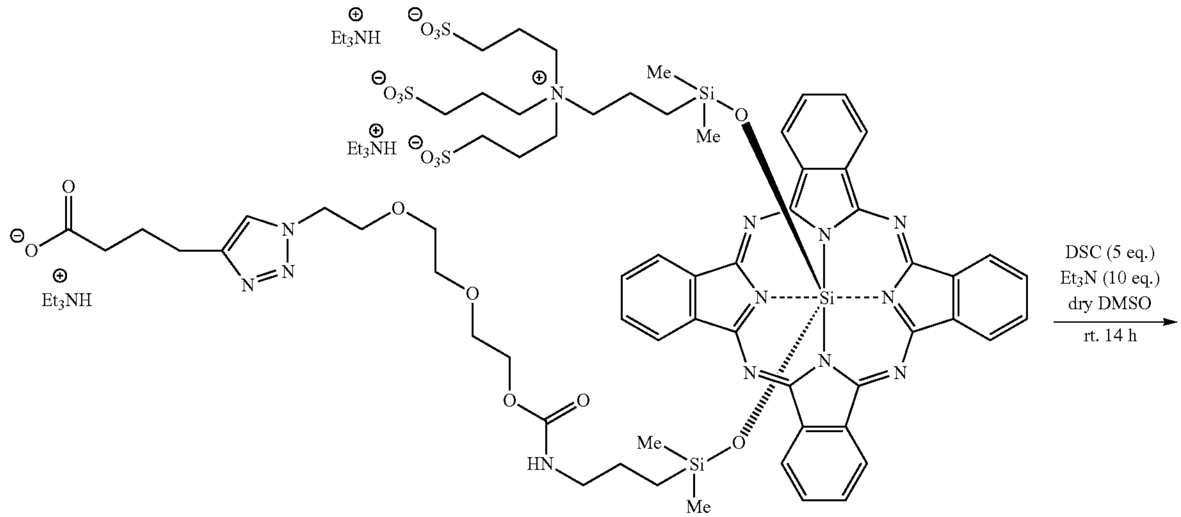

6

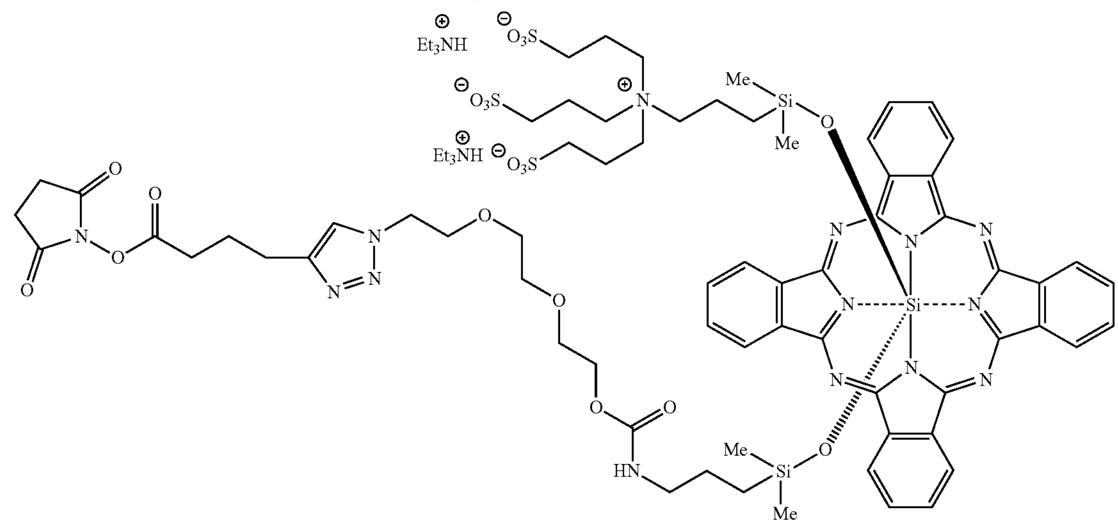

7

N,N'-Disuccinimidyl carbonate (DSC, 1.7 mg, 6.8 μmol), $Et_3N$ (1.4 mg, 14 μmol), and dry dimethyl sulfoxide (500 mL) were added to Compound 6 (2.3 mg, 1.3 μmol), and the obtained mixture was then stirred at room temperature for 14 hours, while shielding the light with an aluminum foil. A precipitate was generated by adding diethyl ether (50 mL) to the reaction solution, and after the removal of a supernatant liquid, the precipitate was washed with diethyl ether (50 mL) to obtain Compound 7. This compound was directly used in the subsequent reaction, without being purified by column chromatography.

Production Example 6: Synthesis of Her-SiPc

[Formula 26]

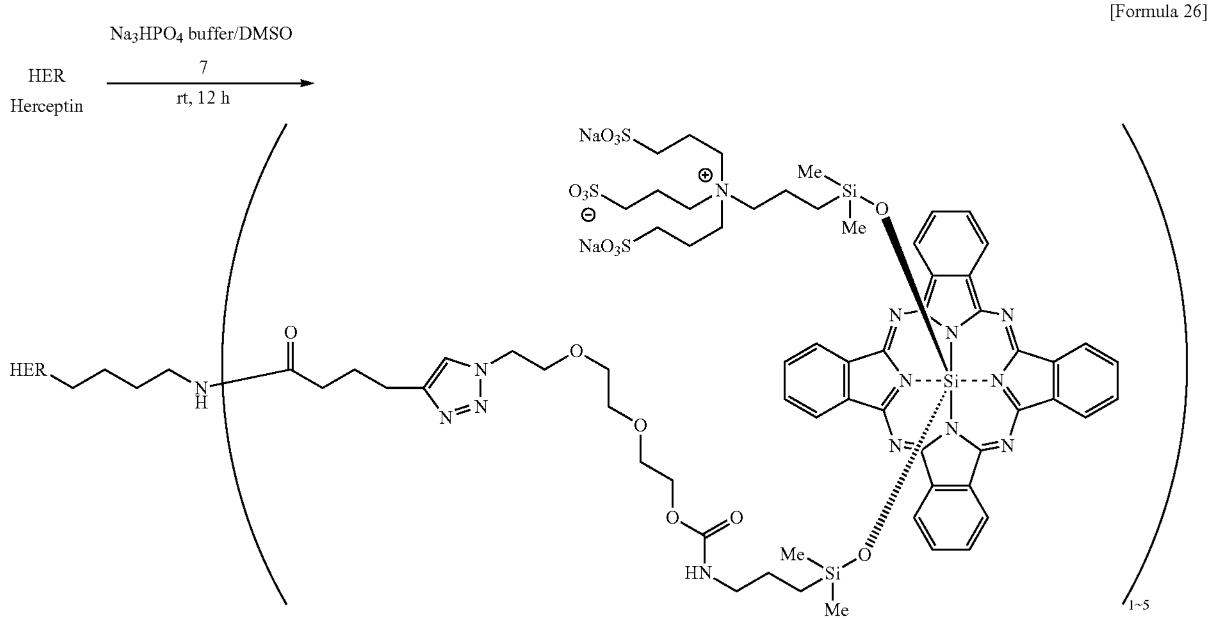

6

Her-SiPc

Herceptin (8.0 mg, Roche) was purified using a phosphate buffer solution (pH 8.0), employing PD Minitrap G-25, to obtain a 7.7 mg/mL Herceptin solution. A dimethyl sulfoxide solution (20 μL) of Compound 7 (88 μg, 50 nmol) was added to 100 μL of the above-obtained solution, and the obtained mixture was then stirred in a dark place at room temperature for 12 hours. Thereafter, the reaction solution was purified with PBS twice, employing PD Minitrap G-25, to obtain a Her-SiPc solution.

<Determination of Drug-Antibody Ratio>

The antibody concentration in a PBS solution of Her-SiPc was determined by a Bradford method (absorbance at 595 nm) (5.28 μM). In addition, a PBS solution of Her-SiPc that had been 8-fold diluted with DMSO was measured in terms of absorption intensity at 673 nm, and thereafter, the concentration of SiPc in the PBS solution of Her-SiPc was calculated (27.4 μM) from the absorbance coefficient at 673 nm of Compound 5 in a DMSO/PBS (7:1) solution. From the thus measured antibody concentration and SiPc concentration, DAR was calculated to be 5.19.

The results obtained by analyzing Herceptin and Her-SiPc according to SDS-PAGE are shown in FIG. 1.

The results obtained by analyzing Herceptin and Her-SiPc according to size exclusion HPLC under the following measurement conditions are shown in FIG. 2.

Measurement Conditions:

Column: Agilent AdvanceBio SEC, 300 Å, 2.7 μm, 7.8×300 mm

Flow rate: 0.5 mL/min

Mobile phase: 1×PBS

Temperature: room temperature

Absorption wavelength: 220 nm

Amount injected: 5 μL

The spectroscopic properties of Her-SiPc in PBS are shown in FIG. 3.

<In Vitro Cytotoxicity Test Using Her-SiPc (1)>

A cytotoxicity test performed using three types of ADC drugs (HerSiPc-1, HerSiPc-2, and HerSiPc-3) shown in Table 1 is described below. As for HerSiPc-2, the HerSiPc-2 produced in Production Example 6 was used herein. HerSiPc-1 and HerSiPc-3 were produced in accordance with the method described in Production Example 6, in which the amount of Compound 7 used was regulated. By increasing the amount of Compound 7, HerSiPc having high DAR is obtained.

HER2 high expression SK-BR-3 cells and HER2low expression MCF7 cells were each seeded on a 96-well plate for cell culture, such that the number of cells became $5\times10^3$ cells/well and the culture solution became 100 μL/well, and thereafter, the cells were cultured overnight. With regard to the three types of ADC drugs, using the culture solution as a solvent, and eight 5-fold dilution series were produced from 2.5E+01 μg/mL. Specifically, they were the eight dilution series, namely, 6.4E-05 μg/mL, 3.2E-04 μg/mL, 1.6E-03 μg/mL, 8.0E-03 μg/mL, 4.0E-02 μg/mL, 2.0E-01 μg/mL, 1.0E+00 μg/mL, and 5.0E+00 μg/mL, from 2.5E+01 μg/mL.

TABLE 1

| Name | DAR |
| --- | --- |
| Her_SiPc-1 | 2.37 |
| Her_SiPc-2 | 5.19 |
| Her_SiPc-3 | 8.63 |

Subsequently, the medium was discarded after completion of the cell culture performed overnight, and the cells were then rinsed with PBS. The prepared ADC drug was added to the resulting cells, and the obtained mixture was then cultured for 24 hours. Twenty-four hours after the culture, the medium was discarded and anew medium was added, and using LED emitting alight with a wavelength of 690±10 nm, the cells were irradiated with alight dose of 100 J/cm$^2$. Thereafter, the cells were cultured for 24 hours, and the two types of cells were then compared in terms of the number of living cells, using Cell Counting Kit-8 (DOJINDO LABORATORIES). The dosage and administration were determined based on the instruction manual, and the cells were incubated at 37° C. in a $CO_2$ incubator for 1.5 hours after addition of the reagent. Thereafter, the absorbance at 450 nm was measured, and a mean value was then calculated. After background correction, the cell growth percentage of the control was defined to be 100%, and the cell growth percentage of individual cells to the control under individual conditions was calculated.

The results of the SK-BR-3 cells are shown in FIG. 4 (with light irradiation) and FIG. 5 (without light irradiation), whereas the results of the MCF7 cells are shown in FIG. 6 (with light irradiation). As shown in FIG. 4 (with light irradiation) and FIG. 5 (without light irradiation), it was confirmed that Her_SiPc has cytotoxicity in a light-dependent, concentration-dependent, and DAR-dependent manner. Moreover, as shown in FIG. 4 (with light irradiation) and FIG. 6 (with light irradiation), it was confirmed that Her_SiPc has cytotoxicity in an antigen expression level-dependent manner.

Production Example 7: Synthesis of Compound 8

[Formula 27]

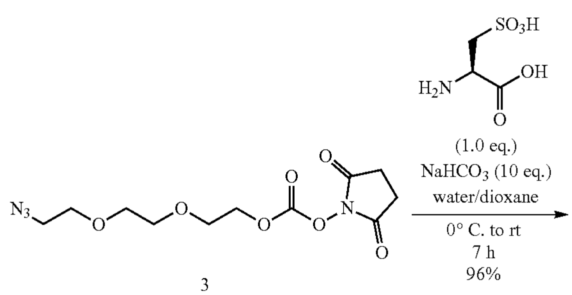

3

-continued

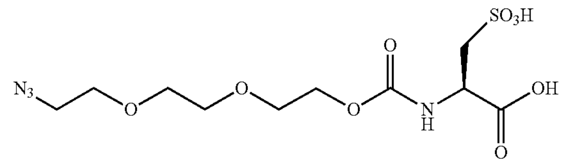

8

A mixed solution of dioxane and water (1:2) (4.5 mL), in which cysteic acid (59.6 mg, 353 μmol) and $NaHCO_3$ (297 mg, 3.53 mmol) had been dissolved, was stirred at 0° C., and thereafter, a dioxane (1.5 mL) solution of Compound 3 (112 mg, 353 μmol) was slowly added to the above-obtained solution, followed by stirring the obtained mixture at room temperature for 7 hours. Thereafter, the solvent was distilled away from the reaction mixture under reduced pressure, and the residue diluted with water/acetonitrile (1:1) to 3000 μL was then purified by reverse phase HPLC (gradient: 0% for 5 min; 0-100% for 30 min $CH_3CN$ in 0.1% trifluoroacetic acid aqueous solution, retention time=16.6 min, YMC—Actus Triart C18, flow rate=10.0 mL/min) to obtain target Compound 8 (126 mg, 340 μmol, 96%, colorless).

$^1$H NMR (500 MHz, $D_2O$): δ 4.18 (dd, J=4.6 Hz, 7.4 Hz, 1H), 3.81-3.78 (m, 2H), 3.31 (t, J=4.0 Hz, 2H), 3.27-3.26 (m, 6H), 3.04 (t, J=4.6 Hz, 2H), 2.99 (dd, J=4.0 Hz, 14.3 Hz), 2.93 (dd, J=7.4 Hz, 14.3 Hz).

LRMS (ESI): m/z 369.05 [M−H]$^-$

Production Example 8: Synthesis of Compound 9

[Fomula 28]

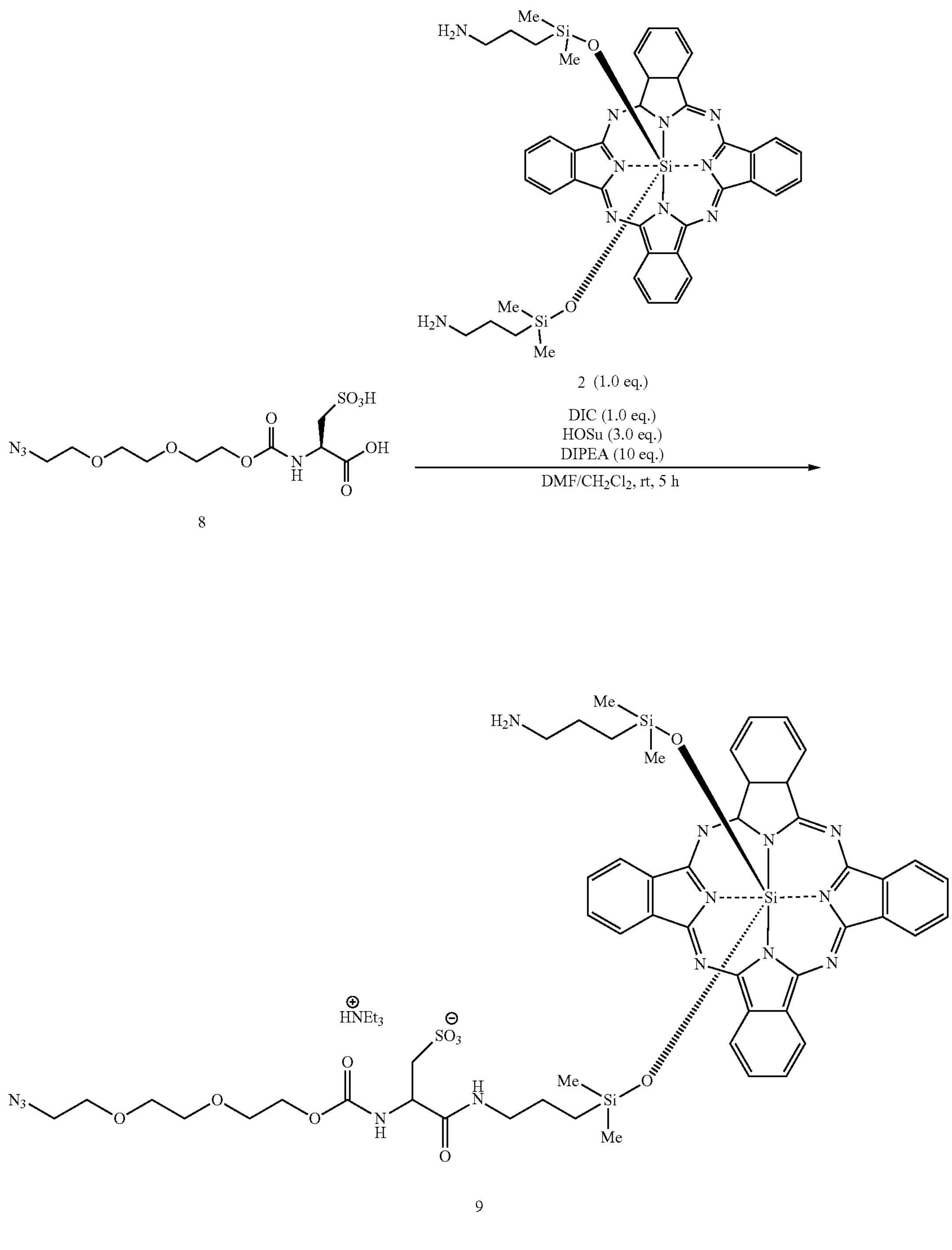

9

DIPEA (72.4 μL, 55.4 mg, 429 μmol), N-hydroxysuccinimide (14.8 mg, 129 μmol), and N,N'-diisopropylcarbodiimide (6.65 μL, 5.41 mg, 42.9 μmol) were added to a dimethylformamide (3 mL) solution of Compound 8 (15.9 mg, 42.9 μmol), and the obtained mixture was then stirred for 1 hour. Thereafter, the obtained solution was slowly added at 0° C. to a dry dichloromethane (27 mL) solution, in which Compound 2 (34.5 mg, 42.9 μmol) had been dissolved, and the thus obtained mixture was then stirred at room temperature for 5 hours, while shielding the light with an aluminum foil. Thereafter, the solvent was distilled away from the reaction mixture under reduced pressure, and the residue was then roughly purified by reverse phase HPLC (gradient: 50% for 5 min; 50-100% for 25 min $CH_3CN$ in 50 mM triethylammonium acetate aqueous solution (pH 7.0), retention time=22.8 min, YMC-Actus Triart C18, flow rate=10.0 mL/min) to obtain target Compound 9, which was directly used in the subsequent reaction.

Production Example 9: Synthesis of Compound 10

[Formula 29]

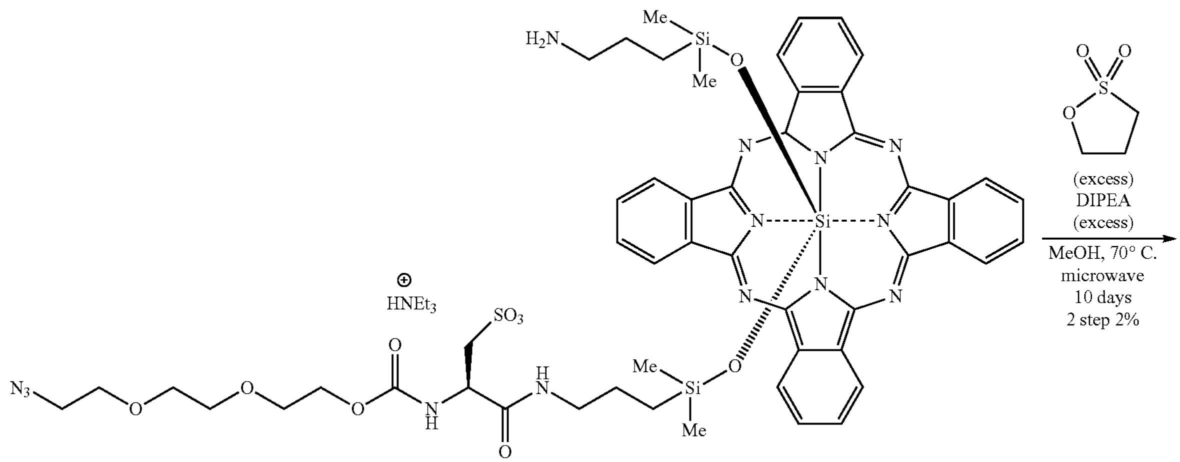

9

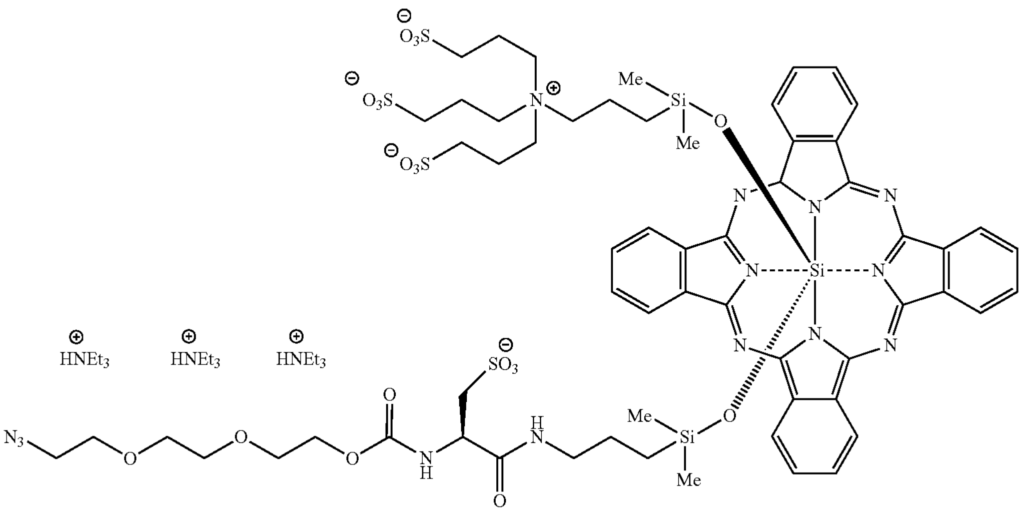

10

1,3-Propanesultone (32.0 μL, 44.5 mg, 364 μmol), DIPEA (91.0 μL, 69.7 mg, 539 mmol), and methanol (10 mL) were added to roughly purified Compound 9 (12.0 mg), and the obtained mixture was then stirred at 70° C. for 3 hours, using a microwave synthesizer (Biotage, Initiator+). Thereafter, 1,3-propanesultone (32.0 μL, 44.5 mg, 364 μmol) and DIPEA (91.0 μL, 69.7 mg, 539 mmol) were further added to the reaction mixture, and the thus obtained mixture was stirred at 70° C. for 3 hours, using the microwave synthesizer (Biotage, Initiator+). Further, this operation was repeated 18 times. Thereafter, the solvent was distilled away from the reaction mixture under reduced pressure, and the residue diluted with water/acetonitrile (1:1) to 6000 μL was divided into two aliquots, which were then purified by reverse phase HPLC (gradient: 50% for 5 min; 50-80% for 25 min; 80-100% for 10 min $CH_3CN$ in 50 mM triethylammonium acetate aqueous solution (pH 7.0), retention time=15.8 min, YMC-Actus Triart C18, flow rate=10 mL/min), so as to obtain target Compound 10 (1.8 mg, 1.0 μmol, 2 step: 2%, dark blue).

LRMS (ESI): m/z 760.80 $[M-2H]^{2-}$

Production Example 10: Synthesis of Compound 11

[Formula 30]

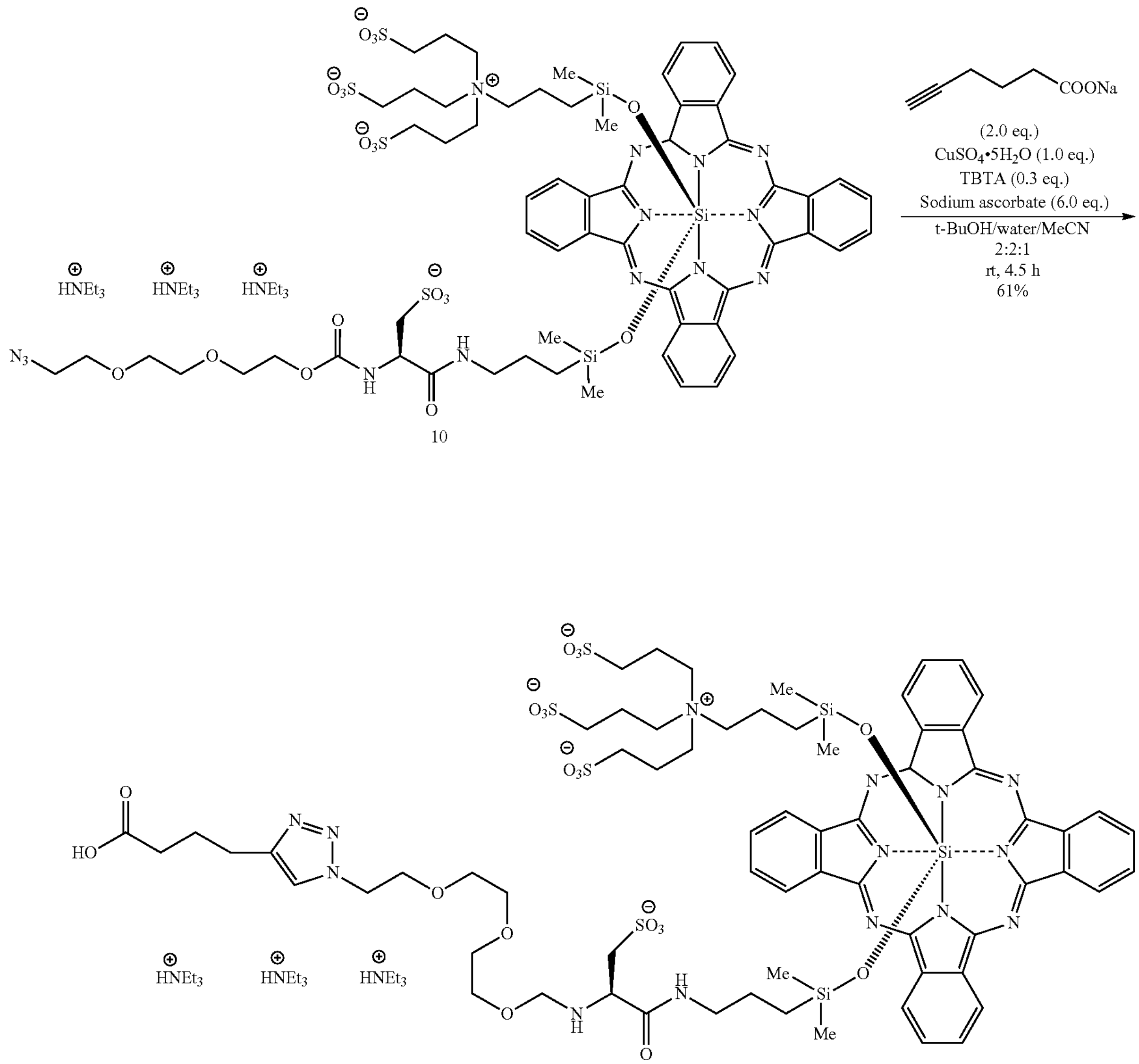

10

11

5-Hexynoic acid sodium salt (0.48 mg, 3.6 μmol), copper sulfate pentahydrate (0.45 mg, 1.8 μmol), tris[(1-benzyl-1H-1,2,3-triazol-4-yl)methyl]amine (0.29 mg, 0.54 μmol), L(+)-ascorbic acid sodium salt (2.2 mg, 11 μmol), t-butanol (300 μL), water (300 μL), and acetonitrile (150 μL) were added to Compound 10 (3.1 mg, 1.8 μmol), and the obtained mixture was then stirred at room temperature for 4.5 hours, while shielding the light with an aluminum foil. Thereafter, the solvent was distilled away from the reaction mixture under reduced pressure, and the residue diluted with water/acetonitrile (1:1) to 3000 μL was purified by reverse phase HPLC (gradient: 30% for 5 min; 30-100% for 40 min $CH_3CN$ in 50 mM triethylammonium acetate aqueous solution (pH 7.0), retention time=16.4 min, YMC-Actus Triart C18, flow rate=10 mL/min), so as to obtain target Compound 11 (2.0 mg, 1.1 μmol, 61%, dark blue).

LRMS (ESI): m/z 816.85 $[M-2H]^{2-}$

Production Example 11: Synthesis of Compound 12

[Formula 31]

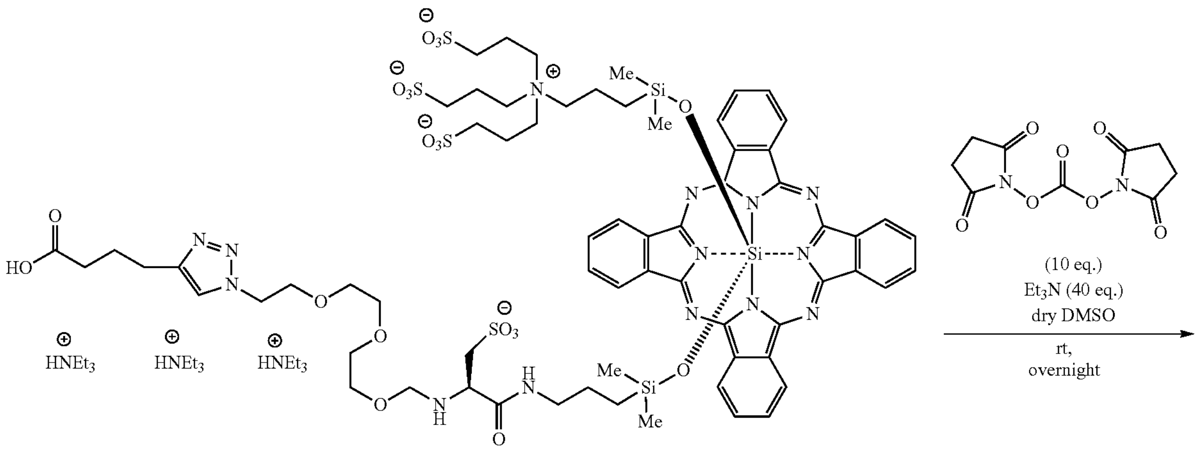

11

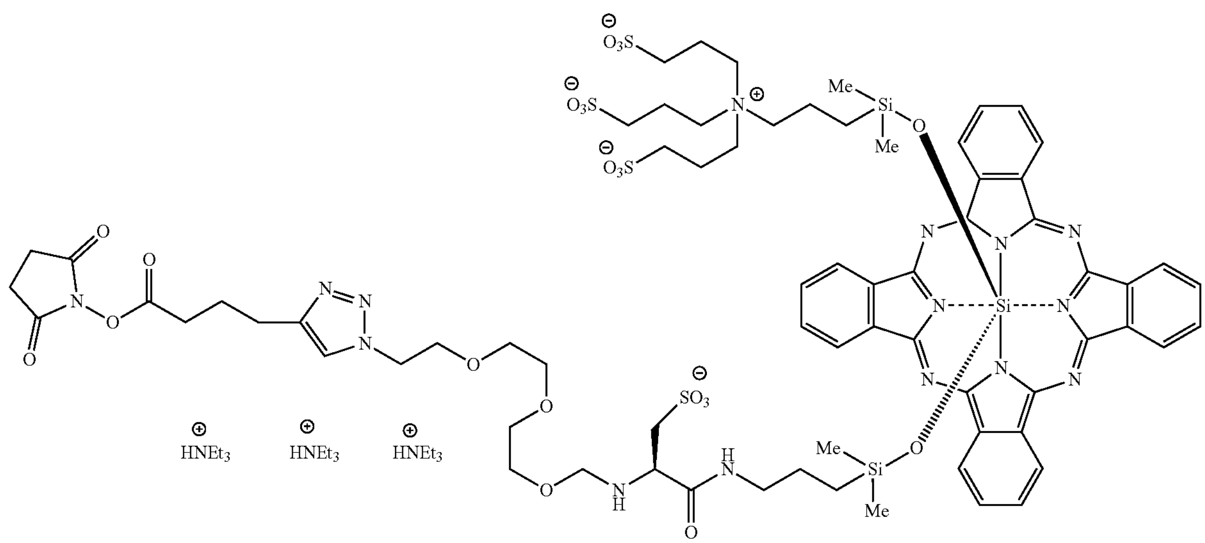

12

N,N'-Disuccinimidyl carbonate (DSC, 2.6 mg, 10 μmol), $Et_3N$ (4.0 mg, 40 μmol), and dry dimethyl sulfoxide (500 μL) were added to Compound 11 (1.9 mg, 1.0 μmol), and the obtained mixture was then stirred at room temperature overnight for 14 hours, while shielding the light with an aluminum foil. Thereafter, a precipitate was generated by adding diethyl ether (50 mL) to the reaction solution, and after the removal of a supernatant liquid, the precipitate was washed with diethyl ether (50 mL) to obtain Compound 12. This compound was directly used in the subsequent reaction, without being purified by column chromatography.

Production Example 12: Synthesis of Compound 13

[Formula 32]

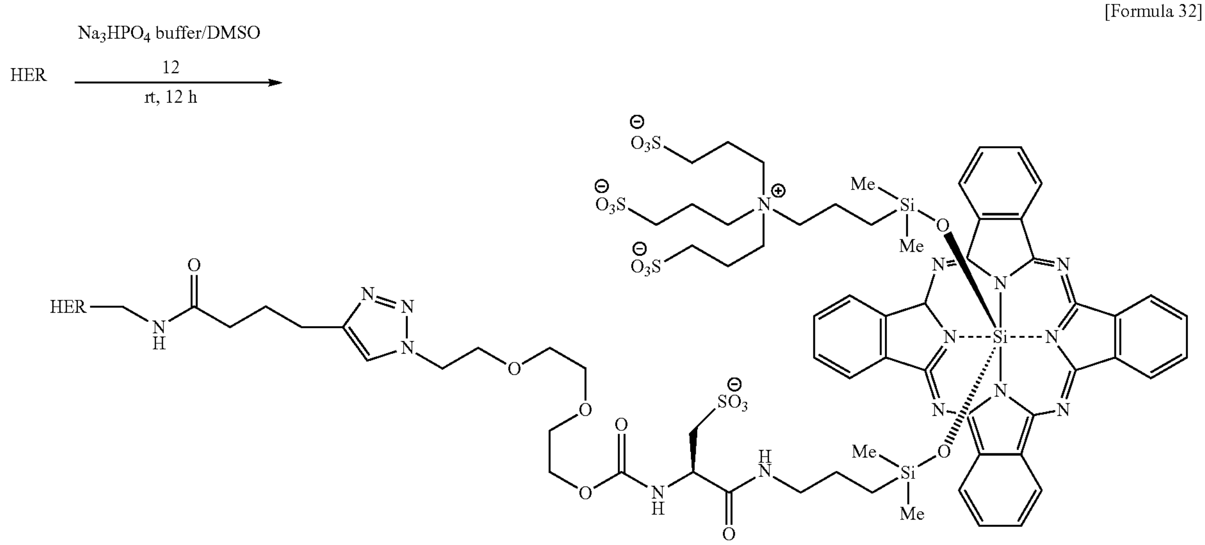

13

Herceptin (8.0 mg, Roche) was purified using a phosphate buffer solution (pH 8.0), employing PD Minitrap G-25, to obtain a 7.7 mg/mL Herceptin solution. A dimethyl sulfoxide solution (20 μL) of Compound 12 (97 g, 50 nmol) was added to 100 μL of the above-obtained solution, and the obtained mixture was then stirred in a dark place at room temperature for 12 hours. Thereafter, the reaction solution was purified with PBS twice, employing PD Minitrap G-25, to obtain a Her-SiPc 13 solution.

Production Example 13: Synthesis of Compound 14

[Formula 33]

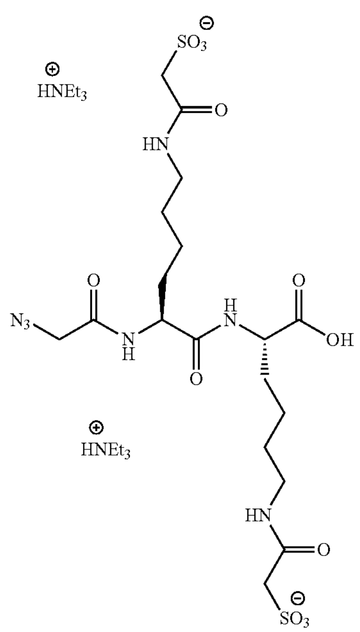

14

Fmoc-Lys(Mmt)-OH (312 mg, 0.50 mmol), Fmoc-Lys (Mmt)-OH (312 mg, 0.50 mmol), and azidoacetic acid (50.5 mg, 0.50 mmol) were successively reacted with Wang Resin (97.0 mg, 0.100 mmol) according to a standard solid phase peptide synthesis method. Thereafter, the reaction mixture was washed with a dichloromethane solution (2 mL) of 1% trifluoroacetic acid/5% triisopropylsilane for 30 seconds, and was then washed with dichloromethane (2 mL) three times. Further, this operation was repeated 19 times. A dimethylformamide solution of sulfoacetic acid (140 mg, 1.0 mmol), N,N'-diisopropylcarbodiimide (126 mg, 1.0 mmol), N-hydroxysuccinimide (230 mg, 2.0 mmol), and Triethylamine (1.01 g, 10 mmol) was stirred at room temperature for 1 minute, and was then mixed with the resin. The obtained mixture was reacted at room temperature for 1 hour, and was then washed with dimethylformamide (2 mL) three times. Further, this operation was repeated twice. The resin was washed with dichloromethane and methanol, and was then dried under reduced pressure. A mixed solution of 95% trifluoroacetic acid/2.5% triisopropylsilane/2.5% water (2 mL) was added to the reaction mixture, and thereafter, the thus obtained mixture was stirred at room temperature for 1 hour, and was then filtered. The filtrate was distilled away under reduced pressure, and diethyl ether was then added to the resultant, so as to precipitate a product. After the removal of a supernatant liquid, the residue was dissolved in water (3000 μL), and was then purified by reverse phase HPLC (gradient: 30% for 5 min; 30-80% for 40 min; 80-100 for 10 min $CH_3CN$ in 0.1% trifluoroacetic acid aqueous solution (pH 7.0), retention time=24.6 min, YMC-Actus Triart C18, flow rate=10 mL/min) to obtain target Compound 14 (27.9 mg, 46 μmol, 46%, colorless).

$^1$H NMR (400 MHz, $D_2O$): δ 4.42-4.38 (m, 2H), 4.11 (s, 2H), 3.85 (s, 4H), 3.32-3.21 (m, 16H), 2.01-1.75 (m, 4H), 1.64-1.59 (m, 4H), 1.50-1.45 (m, 4H), 1.33 (t, J=9.7 Hz, 18H) LRMS (ESI): m/z 599.95 $[M-H]^-$

Production Example 14: Synthesis of Compound 15

[Formula 34]

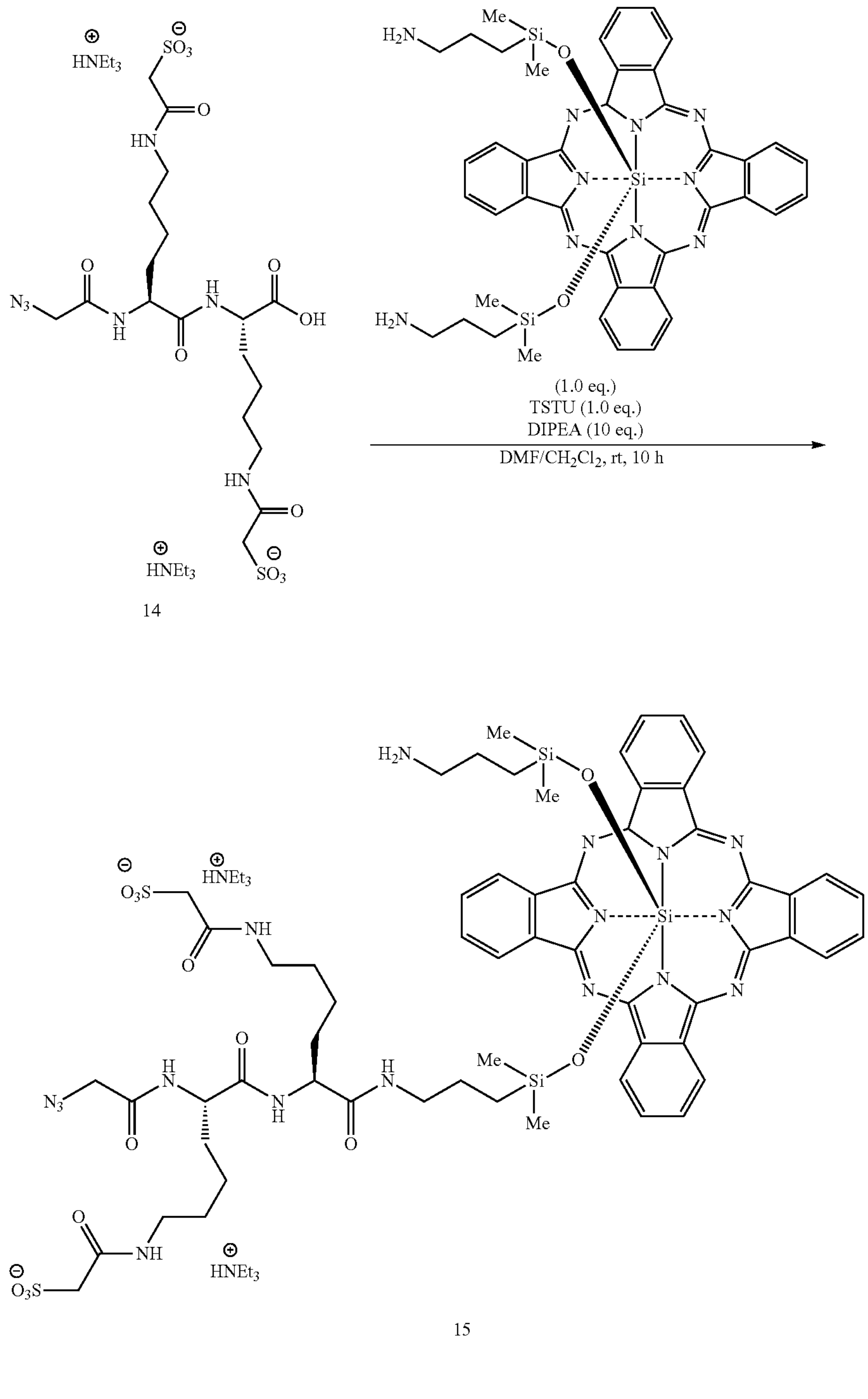

14

15

DIPEA (34.8 μL, 26.6 mg, 206 μmol) and N,N,N',N'-tetramethyl-O—(N-succinimidyl)uronium tetrafluoroborate (TSTU, 6.20 mg, 20.6 mol) were added to a dry dimethylformamide (3 mL) solution of Compound 14 (16.6 mg, 20.6 μmol), and the obtained mixture was then stirred for 1 hour. Thereafter, the obtained solution was slowly added at 0° C. to a dry dichloromethane (27 mL) solution, in which Compound 2 (16.6 mg, 20.6 μmol) had been dissolved, and the thus obtained mixture was then stirred at room temperature for 10 hours, while shielding the light with an aluminum foil. Thereafter, the solvent was distilled away from the reaction mixture under reduced pressure, and the residue was then roughly purified by reverse phase HPLC (gradient: 50% for 5 min; 50-100% for 35 min $CH_3CN$ in 50 mM triethylammonium acetate aqueous solution (pH 7.0), retention time=15.4 min YMC-Actus Triart C18, flowrate=10 mL/min) to obtain target Compound 15, which was directly used in the subsequent reaction.

Production Example 15: Synthesis of Compound 16

[Formula 35]

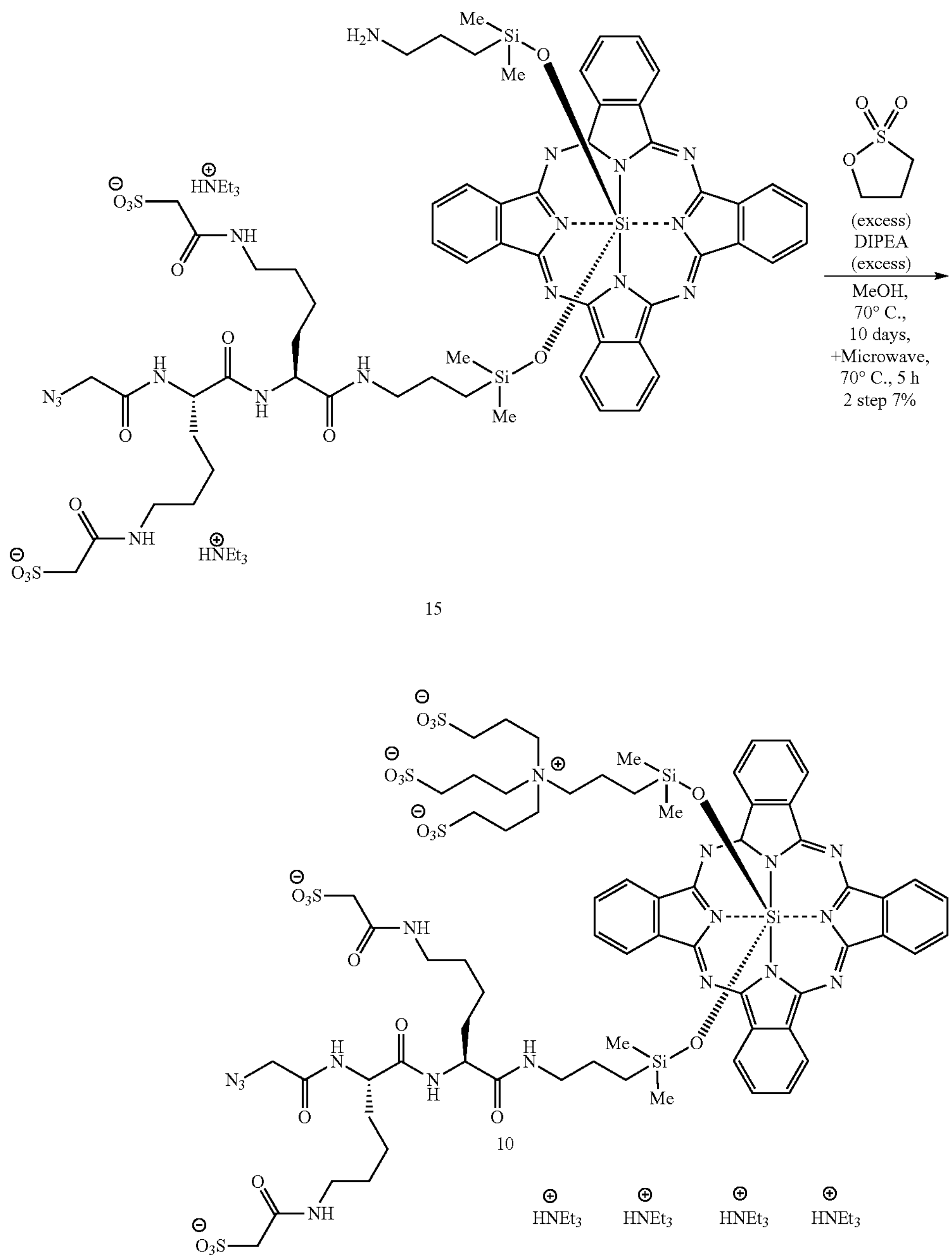

15

16

1,3-Propanesultone (14.6 μL, 20.3 mg, 166 μmol), DIPEA (42.1 μL, 32.2 mg, 250 μmol), and methanol (7 mL) were added to Compound 15 (4.1 mg, 2.6 μmol), followed by stirring. Every day after initiation of the reaction, 1,3-Propanesultone (14.6 μL, 20.3 mg, 166 μmol) and DIPEA (42.1 μL, 32.2 mg, 250 mol) were added to the reaction mixture, and the thus obtained mixture was continuously stirred for 10 days. Thereafter, 1,3-propanesultone (96.0 μL, 134 mg, 1.09 μmol) and DIPEA (273 μL, 209 mg, 1.62 mmol) were further added to the reaction mixture, and then, using a microwave synthesizer (Biotage, Initiator+), the thus obtained mixture was stirred at 70° C. for 5 hours. Thereafter, the solvent was distilled away from the reaction mixture under reduced pressure, and the residue diluted with water/acetonitrile (1:1) to 6000 μL was divided into two aliquots, which were then purified by reverse phase HPLC (gradient: 30% for 5 min; 30-80% for 30 min; 80-100% for 10 min $CH_3CN$ in 50 mM triethylammonium acetate aqueous solution (pH 7.0), retention time=19.2 min, YMC-Actus Triart C18, flow rate=10 mL/min), so as to obtain target Compound 16 (3.00 mg, 1.39 μmol, 7%, dark blue).

LRMS (ESI): m/z 876.30 $[M-2H]^{2-}$

Production Example 16: Synthesis of Compound 17

[Formula 36]

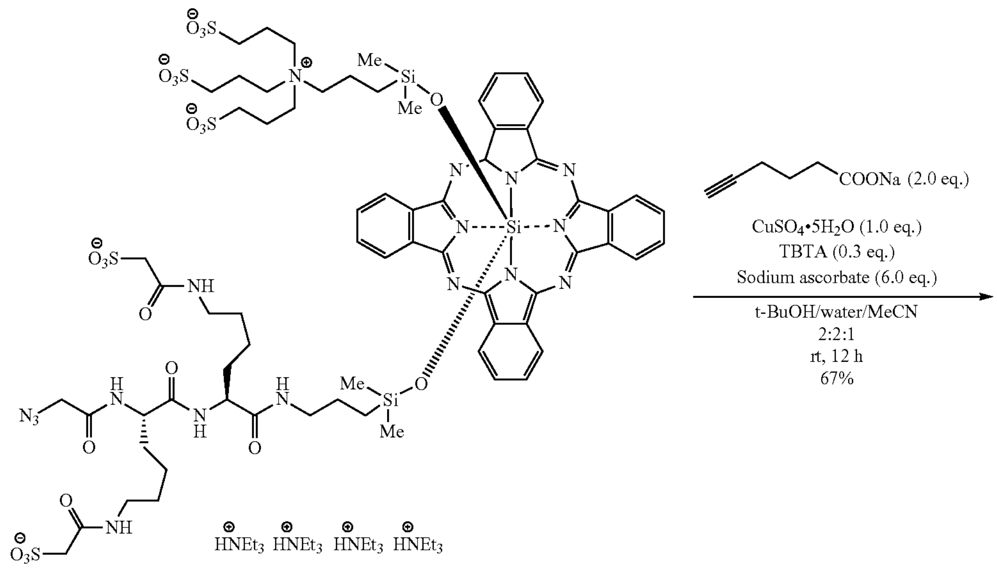

16

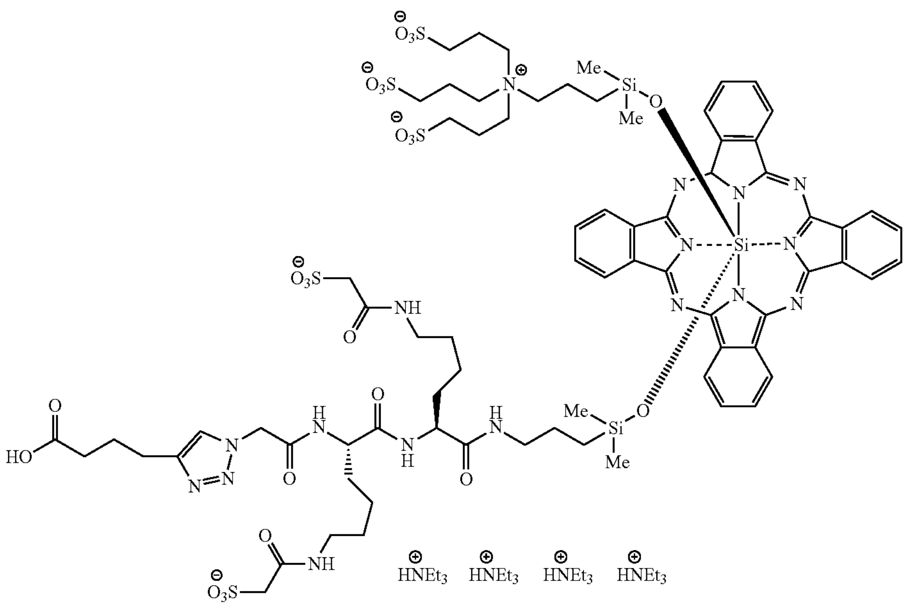

17

5-Hexynoic acid sodium salt (0.39 mg, 2.9 μmol), copper sulfate pentahydrate (0.37 mg, 1.5 μmol), tris[(1-benzyl-1H-1,2,3-triazol-4-yl)methyl]amine (0.23 mg, 0.44 μmol), L(+)-ascorbic acid sodium salt (1.74 mg, 8.76 μmol), t-butanol (300 μL), water (300 μL), and acetonitrile (150 μL) were added to Compound 16 (3.00 mg, 1.46 μmol), and the obtained mixture was then stirred at room temperature for 12 hours, while shielding the light with an aluminum foil. Thereafter, the solvent was distilled away from the reaction mixture under reduced pressure, and the residue diluted with water/acetonitrile (1:1) to 3000 μL was purified by reverse phase HPLC (gradient: 30% for 5 min; 30-100% for 40 min $CH_3CN$ in 50 mM triethylammonium acetate aqueous solution (pH 7.0), retention time=16.4 min, YMC-Actus Triart C18, flow rate=10 mL/min) to obtain target Compound 17 (1.8 mg, 0.83 μmol, 57%, dark blue).

LRMS (ESI): m/z 932.50 $[M-2H]^{2-}$

Production Example 17: Synthesis of Compound 18

[Fomula 37]

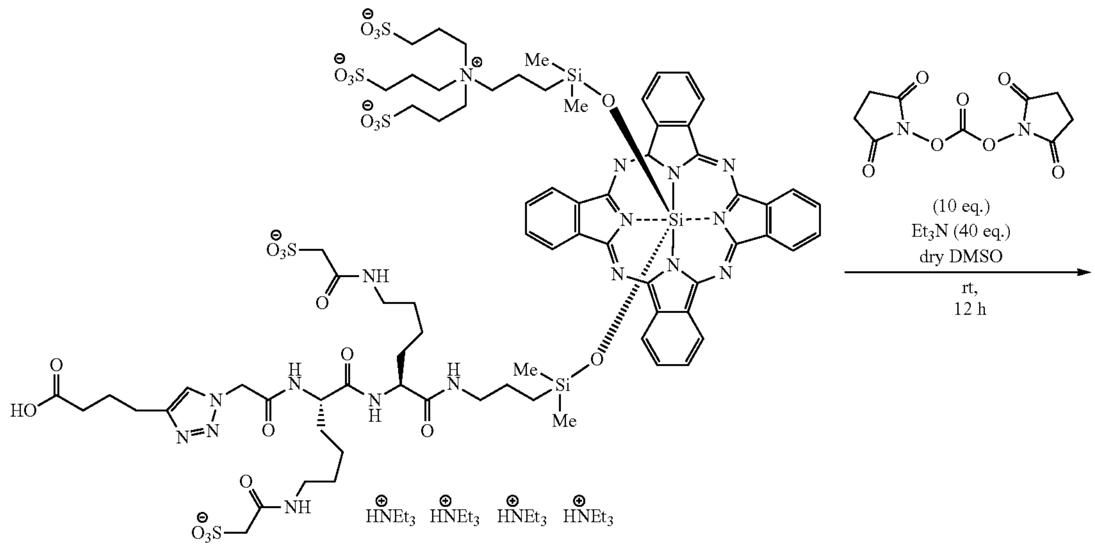

17

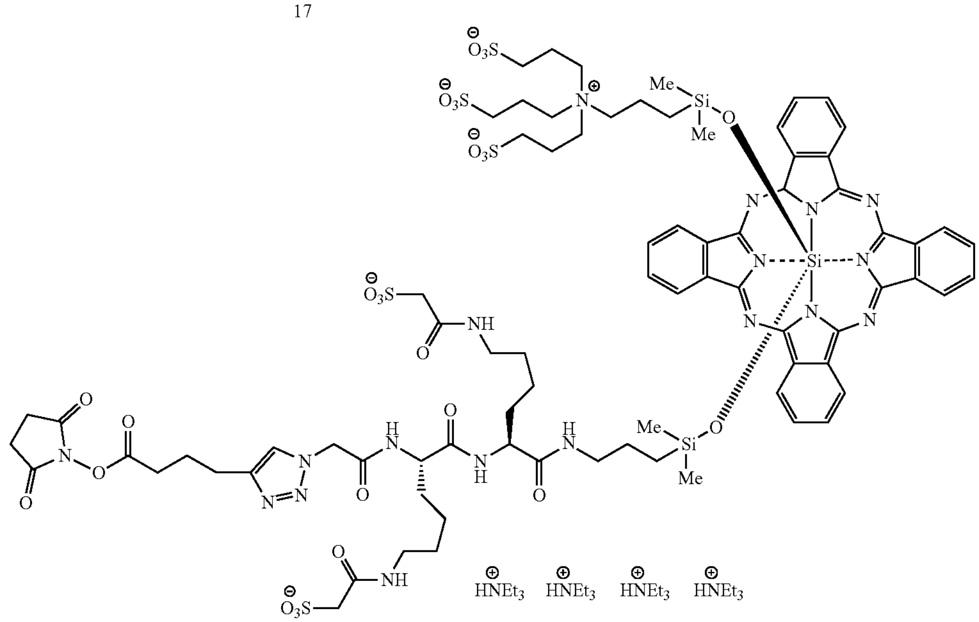

18

N,N'-Disuccinimidyl carbonate (2.1 mg, 8.3 μmol), $Et_3N$ (3.3 mg, 33 μmol), and dry dimethyl sulfoxide (500 μL) were added to Compound 17 (1.8 mg, 0.83 μmol), and the obtained mixture was then stirred at room temperature for 12 hours, while shielding the light with an aluminum foil. Thereafter, a precipitate was generated by adding diethyl ether (50 mL) to the reaction solution, and after the removal of a supernatant liquid, the precipitate was washed with diethyl ether (50 mL) to obtain Compound 18. This compound was directly used in the subsequent reaction, without being purified by column chromatography.

Production Example 18: Synthesis of Compound 19

[Formula 38]

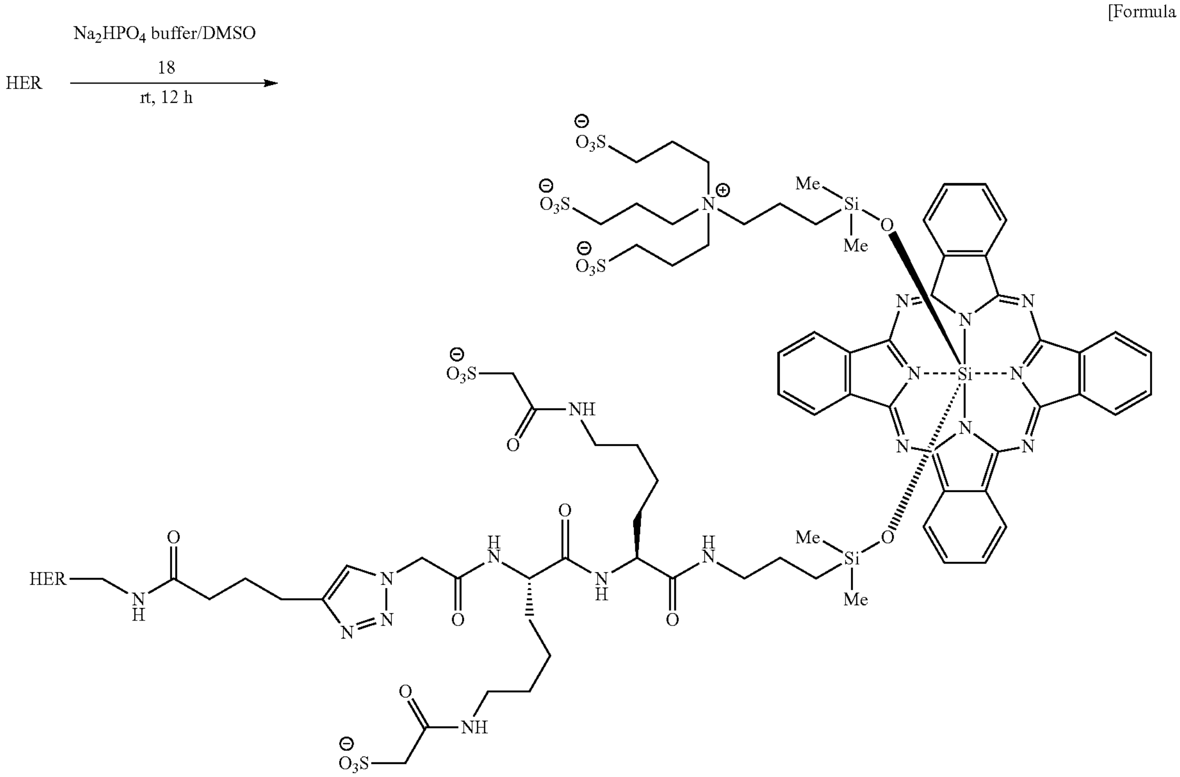

19

Herceptin (8.0 mg, Roche) was purified using a phosphate buffer solution (pH 8.0), employing PD Minitrap G-25, to obtain a 7.7 mg/mL Herceptin solution. A dimethyl sulfoxide solution (20 μL) of Compound 18 (113 μg, 50 nmol) was added to 100 μL of the above-obtained solution, and the thus obtained mixture was then stirred in a dark place at room temperature for 12 hours. Thereafter, the reaction solution was purified with PBS twice, employing PD Minitrap G-25, to obtain a Her-SiPc 19 solution.

<Determination of Drug-Antibody Ratio>

The antibody concentrations in PBS solutions of Compound 13 and Compound 19 were determined by a Bradford method (absorbance at 595 nm) (13: 6.18 μM, 19: 6.29 μM). In addition, a PBS solution of Her-SiPc that had been 8-fold diluted with DMSO was measured in terms of absorption intensity at 673 nm, and thereafter, the concentration of SiPc in the PBS solution of Her-SiPc was calculated from the absorbance coefficient at 673 nm of each of Compound 13 and Compound 19 in a DMSO/PBS (7:1) solution (13: 18.3 μM, 19: 23.4 μM). From the thus measured antibody concentrations and SiPc concentrations, DAR was calculated.

TABLE 2

| Name | DAR |
|---|---|
| Her_SiPc-4 (Compound 13) | 2.96 |
| Her_SiPc-5 (Compound 19) | 3.72 |

<In Vitro Cytotoxicity Test Using Her_SiPc (2)>

A cytotoxicity test, which was performed on Compound 13 (Her SiPc-4) and Compound 19 (Her SiPc-5) using ADC drugs, will be described below. HER2 high expression SK-BR-3 cells and KPL-4 cells were seeded at a cell density of $1\times10^4$ cells/well, so that the culture solution became 100 μL/well, and the cells were then cultured overnight.

Subsequently, dilution series of Compound 13 (Her SiPc-4) and Compound 19 (Her SiPc-5) were prepared, and were then added to the cells, resulting in final concentrations of 5E-05 μg/mL, 5E-04 μg/mL, 5E-03 μg/mL, 5E-02 μg/mL, 5E-01 μg/mL, and 5E+00 μg/mL.

Twenty-four hours later, the medium was discarded, and anew medium was added. Using LED emitting light with a wavelength of 690±10 nm the cells were irradiated with alight dose of 100 J/cm$^2$. Thereafter, the cells were cultured for 24 hours, and the two types of cells were then compared in terms of the number of living cells, using Cell Counting Kit-8 (DOJINDO LABORATORIES). The dosage and administration were determined based on the instruction manual, and the cells were incubated at 37° C. in a $CO_2$ incubator for 1.5 hours after the addition of the reagent. Thereafter, the absorbance at 450 nm was measured, and a mean value was calculated. After background correction, the cell growth percentage of the control was defined to be 100%, and the cell growth percentage of individual cells in the control under individual conditions was calculated.

The results are shown in FIGS. 7 and 8. From the obtained results, it was confirmed that Compound 13 (Her SiPc-4) and Compound 19 (Her SiPc-5) concentration-dependently have cytotoxicity, when they are irradiated with light.

The invention claimed is:

1. A compound represented by the following formula (1) or a salt thereof:

[Formula 1]

(1)

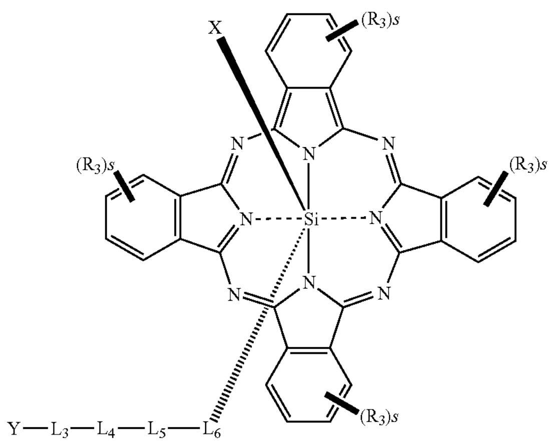

wherein

X represents a substituent having a sulfonic group at the terminus thereof, $L_3$ repesents

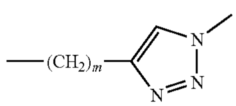

wherein m represents an integer of 1 to 5, $L_4$ represents —$[(CH_2)_p$—$O)]_q$— wherein p and q each independently represent an integer of 1 to 5), or —$(CH_2)_r$— wherein r represents an integer of 1 to 5, $L_5$ represents —CONH—, —NHCO—, —COO—, —OCO—, —CO-$(Xaa)_s$-NH—, or —NH-$(Xaa)_t$-CO— wherein s and t represent an integer of 1 to 10, and Xaa represents an amino acid residue having a hydrophilic group at the terminus of a side chain thereof, $L_6$ represents —$(CH_2)_r$—$Si(R^1)(R^2)$—O— wherein r represents an integer of 1 to 5, and $R^1$ and $R^2$ each independently represent an alkyl group containing 1 to 4 carbon atoms, Y represents an active ester of a carboxyl group, $R_3$ represents an alkoxy group containing 1 to 6 carbon atoms, a halogen atom, —$SR_{11}$, —$SOR_{12}$, —$N(R_{13})(R_{14})$, or —$NO_2$, $R_{11}$, $R_{12}$, $R_{13}$, and $R_{14}$ each independently represent an alkyl group containing 1 to 6 carbon atoms or an alkoxy group containing 1 to 6 carbon atoms, wherein the alkyl group represented by $R_3$, $R_{11}$, $R_{12}$, $R_{13}$ and $R_{14}$, and the alkoxy group represented by $R_{11}$, $R_{12}$, $R_{13}$ and $R_{14}$ may be optionally substituted with a halogen atom, and when a plurality of $R_3$s are present, the plurality of $R_3$s may be identical to or different from one another, and s represents an integer of 0 to 2.

2. The compound or a salt thereof according to claim 1, wherein X represents:

[Formula 2]

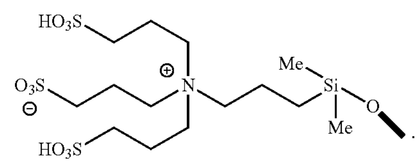

3. Any of the following compounds:

[Formula 4]

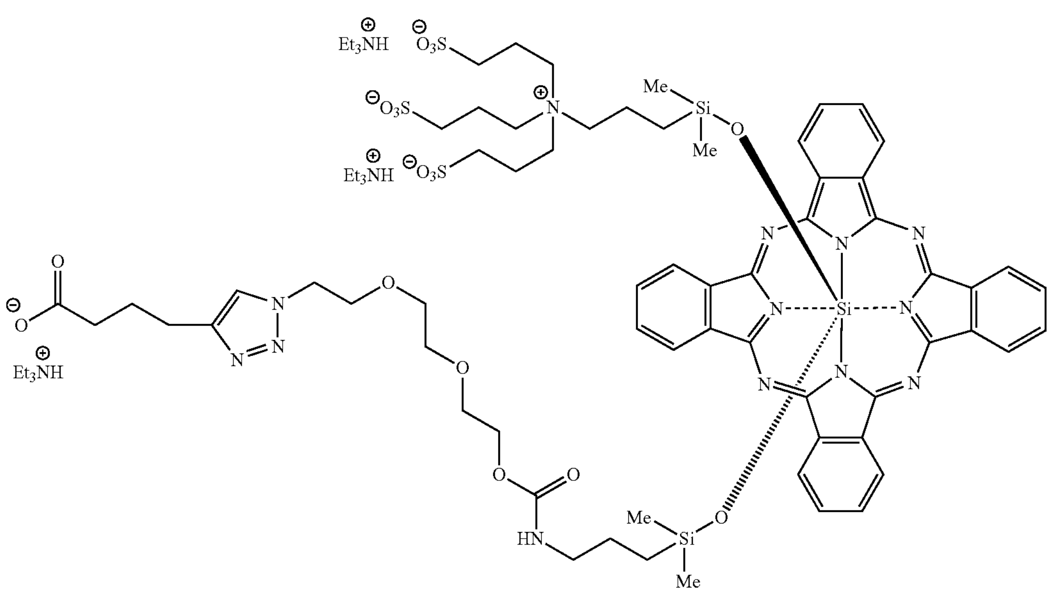

-continued
[Formula 5]
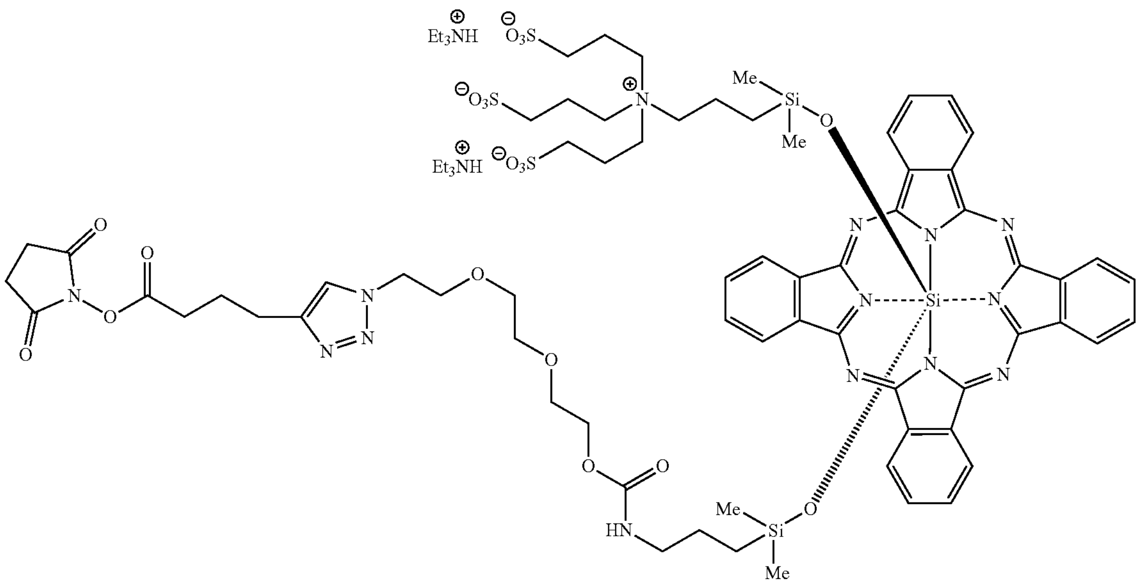
[Formula 6]
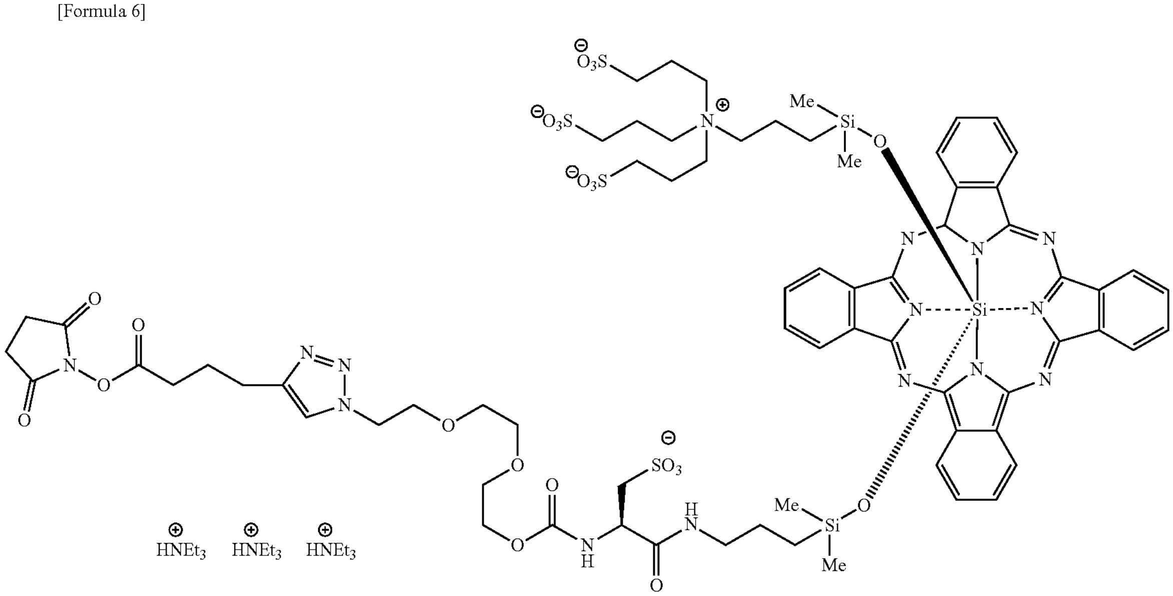

-continued

[Formula 7]

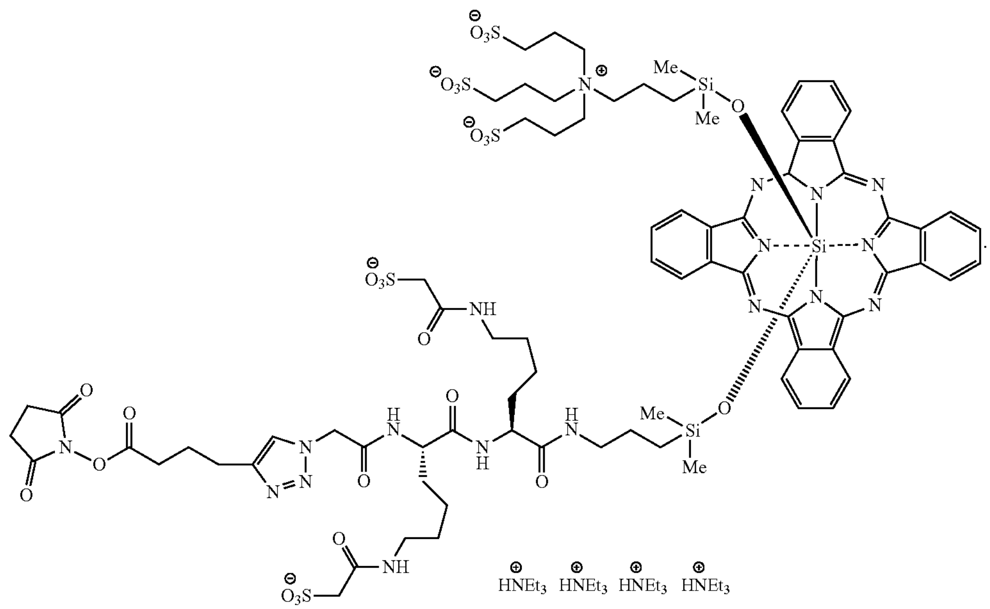

4. A conjugate formed by binding an antibody or a peptide to a group represented by Y in the compound or a salt thereof according to claim 1.

5. The conjugate according to claim 4, wherein the antibody is an anti-HER2 antibody.

6. A conjugate formed by binding an antibody or a peptide to a group represented by Y in the compound or a salt thereof according to claim 1, wherein 1 to 7 molecules of the compound or a salt thereof according to claim 1 bind to 1 molecule of the antibody.

7. A therapeutic agent comprising the conjugate according to claim 4 and a pharmaceutically acceptable carrier.

8. A method for producing the compound or a salt thereof according to claim 1, comprising:

(1) reacting the following Compound 1:

1

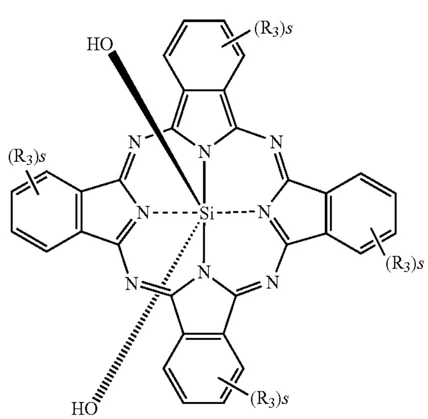

with a compound represented by $L_6$-$NH_2$ to produce the following Compound 2:

2

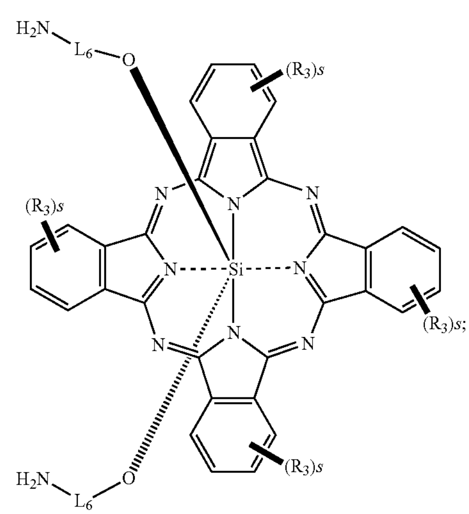

(2) reacting the above Compound 2 with a compound represented by Z1-L4-Z2 wherein Z1 represents an azide group, and Z2 represents an active ester of a carboxyl group, to produce the following Compound 4:

4

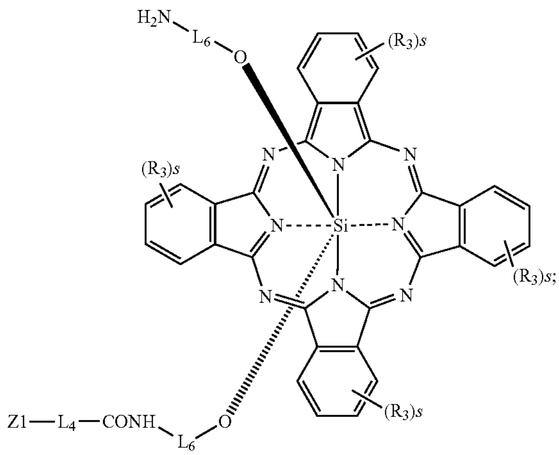

(3) reacting the above Compound 4 with 1,3-propanesultone to produce the following Compound 5:

5

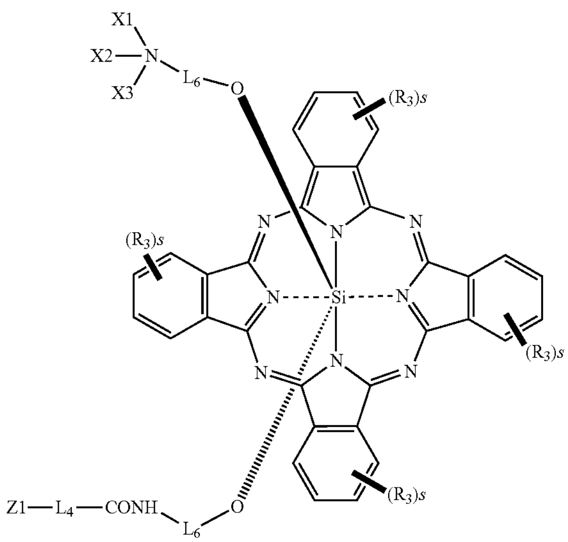

wherein X1, X2, and X3 each represent a group containing a substituent having a sulfonic group at the terminus thereof;

(4) reacting the above Compound 5 with CH≡C—$(CH_2)_t$—COONa wherein t represents an integer of 1 to 5, to produce the following Compound 6 or a salt thereof:

6

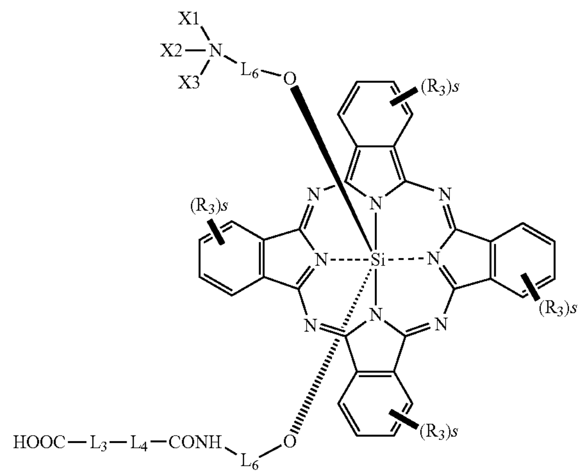

wherein $R_3$ represents, an alkoxy group containing 1 to 6 carbon atoms, a halogen atom, —$SR_{11}$, —$SOR_{12}$, —$N(R_{13})(R_{14})$, or —$NO_2$, $R_{11}$, $R_{12}$, $R_{13}$, and $R_{14}$ each independently represent an alkyl group containing 1 to 6 carbon atoms or an alkoxy group containing 1 to 6 carbon atoms, wherein the alkyl group represented by $R_3$, $R_{11}$, $R_{12}$, $R_{13}$, and $R_{14}$, and the alkoxy group represented by $R_{11}$, $R_{12}$, $R_{13}$, and $R_{14}$, may be optionally substituted with a halogen atom, and when a plurality of $R_3$s are present, the plurality of $R_3$s may be identical to or different from one another, and s represents an integer of 0 to 2; and (5) subjecting the carboxyl group that binds to L3 in the above Compound 6 to active esterification.

* * * * *